United States Patent [19]

Cramp et al.

[11] Patent Number: 6,046,135
[45] Date of Patent: Apr. 4, 2000

[54] 1,3-OXAZIN-4-ONE DERIVATIVES AS HERBICIDES

[75] Inventors: Michael Colin Cramp, Origan, United Kingdom; Yoshihiro Usui; Sachio Kudo, both of Ibaraki-ken, Japan

[73] Assignees: Rhone-Poulenc Agriculture Ltd, Ongar, United Kingdom; Mitsubishi Chemical Corporation, Tokyo, Japan

[21] Appl. No.: 09/077,745

[22] PCT Filed: Dec. 4, 1996

[86] PCT No.: PCT/EP96/05404

§ 371 Date: Sep. 2, 1998

§ 102(e) Date: Sep. 2, 1998

[87] PCT Pub. No.: WO97/21688

PCT Pub. Date: Jun. 19, 1997

[30] Foreign Application Priority Data

Dec. 11, 1995 [GB] United Kingdom .................... 9525265
Nov. 13, 1996 [GB] United Kingdom .................... 9623641

[51] Int. Cl.[7] ............... C07D 265/06; C07D 413/06; C07D 417/06; C07D 413/04; A01N 43/86
[52] U.S. Cl. ....................... 504/223; 544/96; 544/97
[58] Field of Search ..................... 544/96, 97; 504/223

[56] References Cited

U.S. PATENT DOCUMENTS 5,436,224  7/1995  Hamatani et al. ................. 504/223
5,696,054  12/1997  Go et al. ............................ 504/223

FOREIGN PATENT DOCUMENTS 0557691   9/1993   European Pat. Off. .
4-089485  3/1992   Japan .
93/15064  8/1993   WIPO .
94/13665  6/1994   WIPO .
95/10510  4/1995   WIPO .
95/18113  7/1995   WIPO .

OTHER PUBLICATIONS

Derwent Publications Ltd., abstract 92–147592/18 (abstract of JP 04–089485–A), 1992.

*Primary Examiner*—Mukund J. Shah
*Assistant Examiner*—Hong Liu
*Attorney, Agent, or Firm*—Burns, Doane, Swecker & Mathis, L.L.P.

[57] ABSTRACT

1,3-Oxazin-4-one derivatives of formula (I):

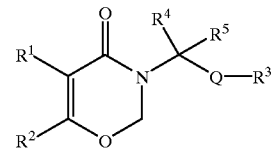

wherein Q represents —C(=O)—, —CH(OH)— or —C(OR$^{11}$)(OR$^{11}$)—, in which R$^{11}$ represents lower alkyl; or the two groups —OR$^{11}$, together with the carbon atom to which they are attached, form a five or six membered cyclic ketal group; and their use as herbicides.

41 Claims, No Drawings

1,3-OXAZIN-4-ONE DERIVATIVES AS HERBICIDES

This application is a 371 of PCT/EP96/05404, filed on Dec. 4, 1996.

This invention relates to novel 1,3-oxazin-4-one derivatives, herbicidal compositions containing the same, and novel intermediates for preparing the same.

Certain types of 1,3-oxazin-4-one derivatives, such as 2,3-dihydro-6-methyl-3-(1-methyl-1-phenylethyl)-5-phenyl-4H-1,3-oxazin-4-one, and their herbicidal activities are disclosed in for example International Patent Publication No. WO 93/15064. However, the compounds described in the above-mentioned publication do not have a ketone or alcohol functionality in the group attached to the nitrogen atom at the 3-position of a 1,3-oxazine ring.

According to the present invention, there are provided 1,3-oxazin-4-one derivatives of formula I:

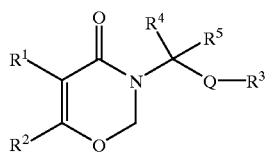

(I)

wherein:

$R^1$ represents phenyl optionally substituted by from one to five groups which may be the same or different selected from halogen, hydroxy, lower alky, lower haloalkyl, lower alkoxy, lower haloalkoxy, —S(O)$_n$R$^7$, —CO$_2$R$^7$, —COR$^7$, cyano, nitro, —O(CH$_2$)$_q$CO$_2$R$^7$ and phenoxy;

a five to seven membered heteroaromatic ring having from one to four ring heteroatoms which may be the same or different selected from nitrogen, oxygen and sulphur, said ring being optionally substituted by from one to four groups which may be the same or different selected from halogen, hydroxy, lower alkyl lower haloalkyl, lower alkoxy, lower haloalkoxy, —S(O)$_n$R$^7$, —CO$_2$R$^7$, —COR$^7$, cyano, nitro, —O(CH$_2$)$_q$CO$_2$R$^7$ and phenoxy;

or a straight- or branched-chain optionally halogenated alkyl, alkenyl or alkynyl group containing up to ten carbon atoms;

$R^2$ represents:

a hydrogen atom; or a straight- or branched-chain alkyl group containing from one to ten carbon atoms which is optionally substituted by one or more groups $R^8$ which may be the same or different;

a straight- or branched-chain optionally halogenated alkenyl or alkynyl group having up to ten carbon atoms;

or a group selected from cyano, —CHO, —COR$^7$, —CO$_2$H, —CO$_2$R$^7$, —COSR$^7$, —CONR$^9$R$^{10}$, —CH=NOH, —CH=NOR$^7$, —CH=NOCOR$^7$, —CH=NNR$^9$R$^{10}$, —CH$_2$CN, —CH$_2$NO$_2$ and oxiranyl;

$R^3$ represents —(CH$_2$)$_r$—(phenyl or naphthyl optionally substituted by from one to five groups which may be the same or different selected from halogen, hydroxy, lower alkyl lower haloalkyl, lower alkoxy, lower haloalkoxy, —S(O)$_n$R$^6$, —CO$_2$R$^6$, —COR$^6$, cyano, nitro, —O(CH$_2$)$_q$CO$_2$R$^6$, phenoxy and —SF$_5$);

—(CH$_2$)$_s$—five to seven membered heteroaromatic ring having from one to four ring heteroatoms which may be the same or different selected from nitrogen, oxygen and sulphur, said ring being optionally fused to a phenyl ring or to a second five to seven membered heteroaromatic ring having from one to four heteroatoms which may be the same or different selected from nitrogen, oxygen and sulphur, to form a bicyclic ring system, the monocyclic ring or either ring in the bicyclic system being optionally substituted by from one to four groups which may be the same or different selected from halogen, hydroxy, lower alkyl, lower haloalkyl, lower alkoxy, lower haloalkoxy, —S(O)$_n$R$^6$, —CO$_2$R$^6$, —COR$^6$, cyano, nitro, —O(CH$_2$)$_q$CO$_2$R$^6$ and phenoxy);

a straight- or branched-chain optionally halogenated alkyl, alkenyl or alkynyl group containing up to ten carbon atoms;

a straight- or branched-chain optionally halogenated alkyl, alkenyl or alkynyl group containing up to ten carbon atoms which is substituted by cycloalkyl containing from three to six carbon atoms; or cycloalkyl containing from three to six carbon atoms or cycloalkenyl containing five or six carbon atoms, the ring systems of which are optionally substituted by a group $R^6$ or one or more halogen atoms which may be the same or different;

$R^4$ and $R^5$ independently represent lower alkyl;

$R^6$ and R7 independently represent lower alkyl or lower haloalkyl;

n represents zero, one or two;

q represents one or two;

r represents zero, one or two; s represents zero or one;

$R^8$ is halogen, —OH, —OR$^7$, —OCOR$^7$, —S(O)$_n$R$^7$, —NR$^9$R$^{10}$ or azide;

$R^9$ and $R^{10}$ independently represent hydrogen, lower alkyl or lower haloalkyl;

Q represents —C(=O)—, —CH(OH)— or —C(OR$^{11}$)(OR$^{11}$)—; in which $R^{11}$ represents lower alkyl; or the two groups —OR$^{11}$, together with the carbon atom to which they are attached, form a five or six membered cyclic ketal group;

and agriculturally acceptable salts thereof, which possess valuable properties.

By the term "agriculturally acceptable salts" is meant salts, the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triehanolamine, octylamine, morpholine and dioctylmethylamine) salts. Suitable acid addition salts, e.g. formed by compounds of formula I containing an amino group, include salts with inorganic acids, for example hydrochlorides, sulphates, phosphates and nitrates and salts with organic acids for example acetic acid.

In certain cases the groups $R^1$ to $R^{11}$ may give rise to stereoisomers and geometric isomers. All such forms are embraced by the present invention.

In the description unless otherwise specified the following terms are generally defined thus:

'lower alkyl' means a straight- or branched-chain alkyl group having one to six carbon atoms;

'lower haloalkyl' means a straight- or branched-chain alkyl group having one to six carbon atoms, substituted by one or more halogens;

'lower alkoxy' means a straight- or branched-chain alkoxy group having one to six carbon atoms;

'lower haloalkoxy' means a straight- or branched-chain alkoxy group having one to six carbon atoms, substituted by one or more halogens;

'halogen' means a fluorine, chlorine, bromine or iodine atom.

In the description that follows a number of preferred classes (because of their herbicidal properties) of compounds of formula I above are disclosed.

Compounds of formula (I) in which $R^3$ is —$(CH_2)_r$—(phenyl optionally substituted by from one to five groups which may be the same or different selected from halogen, hydroxy, lower alkyl lower haloalkyl, lower alkoxy, lower haloalkoxy, —$S(O)_nR^6$, —$CO_2R^6$, —$COR^6$, cyano, nitro, —$O(CH_2)_qCO_2R^6$, and phenoxy);

—$(CH_2)_s$—(five to seven membered heteroaromatic ring having from one to four ring heteroatoms which may be the same or different selected from nitrogen, oxygen and sulphur, said ring being optionally fused to a phenyl ring or to a second five to seven membered heteroaromatic ring having from one to four heteroatoms which may be the same or different selected from nitrogen, oxygen and sulphur, to form a bicyclic ring system, the monocyclic ring or either ring in the bicyclic system being optionally substituted by from one to four groups which may be the same or different selected from halogen, hydroxy, lower alkyl, lower haloalkyl, lower alkoxy, lower haloalkoxy, —$S(O)_nR^6$, —$CO_2R^6$, —$COR^6$, cyano, nitro, —$O(CH_2)_qCO_2R^6$ and phenoxy); or a straight- or branched-chain optionally halogenated alkyl, alkenyl or alkynyl group containing up to ten carbon atoms; or cycloalkyl containing from three to six carbon atoms which is optionally substituted by a group $R^6$ or one or more halogen atoms which may be the same or different;

r is zero or one; and $R^8$ is not azide; are preferred.

Compounds of formula (I) above in which $R^1$ represents phenyl or thienyl optionally substituted by one or more groups selected from halogen, lower alkyl and lower haloalkyl are preferred. Most preferably $R^1$ represents phenyl.

A further preferred class of compounds of formula I above are those wherein $R^2$ represents a straight- or branched-chain alkyl group having from one to six carbon atoms, most preferably methyl.

Compounds of formula (I) above in which $R^4$ and $R^5$ each represent methyl are especially preferred.

Compounds of formula (I) above in which Q represents —C(=O)— are especially preferred because of their herbicidal activity. Compounds of formula (I) above in which Q is —CH(OH)— generally have a lower level of herbicidal activity than the corresponding compounds of formula (I) in which Q is —C(=O)—, and are also useful as intermediates in the preparation of such compounds.

Compounds of formula (I) above in which $R^3$ is cyclopentyl are preferred due to their high activity against weeds found in rice.

Compounds of formula (I) above in which $R^3$ is n-butyl or butenyl (e.g. 3-butenyl) are also preferred due to their efficacy against difficult to control weeds found in cereals, such as blackgrass (*Alopecurus myosuroides*).

A particularly preferred class of compounds of formula (I) above are those wherein:

$R^1$ represents phenyl optionally substituted by halogen;
$R^2$, $R^4$ and $R^5$ each represent methyl;
Q represents —C(=O)—; and
$R^3$ represents:

—$(CH_2)_r$-(phenyl optionally substituted by one or two groups selected from halogen and an optionally halogenated alkyl group containing one or two carbon atoms); or a straight- or branched-chain alkyl, alkenyl or alkynyl group containing up to four carbon atoms;
and r is zero or one.

A further particularly preferred class of compounds of formula (I) above are those wherein:

$R^1$ represents:
phenyl or thienyl optionally substituted by halogen or methyl;
$R^2$, $R^4$ and $R^5$ each represent methyl;
Q represents —C(=O)—;
$R^3$ represents —$(CH_2)_r$—(phenyl optionally substituted by one or two groups selected from halogen or an optionally halogenated alkyl group containing one or two carbon atoms);

a straight- or branched-chain alkyl or alkenyl group containing up to six carbon atoms;
or cycloalkyl containing from three to six carbon atoms; and r is zero or one.

A further particularly preferred class of compounds of formula (I) above are those having one or more of the following features:

$R^1$ represents:
phenyl or thienyl optionally substituted by halogen or methoxy;
$R^2$, $R^4$ and $R^5$ each represent methyl;
Q represents —C(=O)—;
$R^3$ represents:

—$(CH_2)_r$—(phenyl group optionally substituted by one or two groups selected from halogen or methyl);

thienyl, furyl, benzthiazolyl or pyridyl, optionally substituted by halogen or (optionally halogenated) methyl;

a straight- or branched-chain optionally halogenated alkyl, alkenyl or alkynyl group containing up to eight carbon atoms; or cycloalkyl containing from three to six carbon atoms; and
r is zero or one.

The following compounds of formula (I) above in which $R^4$ and $R^5$ are methyl and Q is —C(=O)— form part of the present invention. In the table below 'Ph' means phenyl, 'Me' means methyl, 'Et' means ethyl, 'Pr' means propyl and 'Bu' means butyl. Where subscripts are omitted after atoms it will be understood that they are intended, for example CH=CH2 means —CH=$CH_2$ etc.

| Cpd. No. | $R^1$ | $R^2$ | $R^3$ |
|---|---|---|---|
| 1 | Ph | Me | i-Pr |
| 2 | Ph | Me | n-Bu |
| 3 | Ph | Me | 3,5-F2 Ph |
| 4 | Ph | Me | 2-F-5-CF3 phenyl |
| 5 | Ph | Me | 3-Cl benzyl |
| 6 | Ph | Me | 3-CF3 benzyl |
| 7 | Ph | Me | CH2CH=CH2 |
| 8 | Ph | Me | CH=CH2 |
| 9 | 2-F phenyl | Me | 4-F phenyl |
| 10 | Ph | Me | ethynyl |
| 11 | 2-F phenyl | Me | 2-Me phenyl |
| 12 | 2-F phenyl | Me | 4-F-3-Me phenyl |
| 13 | Ph | Me | 2-Me phenyl |
| 14 | Ph | Me | 4-F phenyl |
| 15 | Ph | Me | 4-F-3-Me phenyl |
| 16 | Ph | Me | Ph |
| 17 | Ph | Me | 2-Cl phenyl |
| 18 | Ph | Me | 3-Cl phenyl |
| 19 | Ph | Me | 4-Cl phenyl |
| 20 | Ph | Me | 3-CF3 phenyl |
| 21 | Ph | Me | 3,5-Cl2 phenyl |
| 22 | Ph | Me | 2,5-F2 phenyl |
| 23 | Ph | Me | 2-pyridyl |
| 24 | Ph | Me | 4-pyridyl |
| 25 | Ph | Me | 4-methylthiazol-2-yl |
| 26 | Ph | Me | 5-chlorothiazol-2-yl |
| 27 | Ph | Me | Me |
| 28 | Ph | Me | Et |

-continued

| Cpd. No. | R¹ | R² | R³ |
|---|---|---|---|
| 29 | Ph | Me | n-Pr |
| 30 | Ph | Me | i-Bu |
| 31 | Ph | Me | cyclopropyl |
| 32 | Ph | Me | sec-butyl |
| 33 | Ph | Me | cyclobutyl |
| 34 | Ph | Me | n-pentyl |
| 35 | Ph | Me | n-hexyl |
| 36 | Ph | Me | cyclohexyl |
| 37 | Ph | Me | n-heptyl |
| 38 | Ph | Me | n-octyl |
| 39 | Ph | Me | 3,5-Cl2 benzyl |
| 40 | 2-F phenyl | Me | 3,5-Cl2 phenyl |
| 41 | 2-F phenyl | Me | 3-CF3 phenyl |
| 42 | 2-F phenyl | Me | 4-methylthiazol-2-yl |
| 43 | 2-F phenyl | Me | n-butyl |
| 44 | 2-F phenyl | Me | cyclobutyl |
| 45 | 2-F phenyl | Me | 3-Cl benzyl |
| 46 | 2-OMe phenyl | Me | 3,5-Cl2 phenyl |
| 47 | 2-OMe phenyl | Me | 3-CF3 phenyl |
| 48 | 2-OMe phenyl | Me | n-butyl |
| 49 | 2-OMe phenyl | Me | n-propyl |
| 50 | 2-OMe phenyl | Me | 2-pyridyl |
| 51 | 3-Cl phenyl | Me | n-butyl |
| 52 | 3-Cl phenyl | Me | 3,5-Cl2 phenyl |
| 53 | 2-thienyl | Me | 3,5-Cl2 phenyl |
| 54 | 2-thienyl | Me | 3-CF3 phenyl |
| 55 | 2-thienyl | Me | 4-methylthiazol-2-yl |
| 56 | 2-thienyl | Me | n-butyl |
| 57 | 2-thienyl | Me | cyclobutyl |
| 58 | 2-thienyl | Me | 3-Cl benzyl |
| 59 | 2-furyl | Me | 3,5-Cl2 phenyl |
| 60 | iso-butyl | Me | 3,5-Cl2 phenyl |
| 61 | iso-butyl | Me | n-butyl |
| 62 | iso-butyl | Me | 3-Cl benzyl |
| 63 | 4-methylpent-1-yn-1-yl | Me | 3-CF3 phenyl |
| 64 | 4-methylpent-1-yn-1-yl | Me | n-butyl |
| 65 | 4-methylpent-1-yn-1-yl | Me | 4-pyridyl |
| 66 | 4-methylpent-1-yn-1-yl | Me | ethyl |
| 67 | 2-methylprop-1-en-1-yl | Me | 3,5-Cl2 phenyl |
| 68 | 2-methylprop-1-en-1-yl | Me | n-butyl |
| 69 | Ph | CH2F | 3,5-Cl2 phenyl |
| 70 | Ph | CH2F | n-butyl |
| 71 | Ph | CH2F | 3-Cl benzyl |
| 72 | Ph | CH2F | 5-chlorothiazol-2-yl |
| 73 | Ph | CH2OMe | 3-CF3 phenyl |
| 74 | Ph | CH2OMe | iso-butyl |
| 75 | Ph | CH2OMe | 3,5-Cl2 benzyl |
| 76 | Ph | CH2OMe | cyclohexyl |
| 77 | Ph | CH2SMe | 3,5-Cl2 phenyl |
| 78 | Ph | CH2SMe | n-butyl |
| 79 | Ph | CH2SMe | 3-Cl benzyl |
| 80 | Ph | CH2SMe | 5-chlorothiazol-2-yl |
| 81 | Ph | CHF2 | 3-CF3 phenyl |
| 82 | Ph | CHF2 | iso-butyl |
| 83 | Ph | CHF2 | 3,5-Cl2 benzyl |
| 84 | Ph | CHF2 | cyclohexyl |
| 85 | Ph | CH=NOMe | 3,5-Cl2 phenyl |
| 86 | Ph | CH=NOMe | n-butyl |
| 87 | 2-F phenyl | CH2SMe | 3,5-Cl2 phenyl |
| 88 | 2-F phenyl | CHOMe | n-butyl |
| 89 | 2-thienyl | CH2F | 3,5-Cl2 phenyl |
| 90 | Ph | Me | t-Bu |
| 91 | Ph | Me | 2-thienyl |
| 92 | Ph | Me | 2-furyl |
| 93 | Ph | Me | 2-benzthiazolyl |
| 94 | Ph | Me | 3,4-Cl2-benzyl |
| 95 | Ph | Me | 3,5-Me2-benzyl |
| 96 | Ph | Me | 4-Cl-benzyl |
| 97 | Ph | Me | cyclopentyl |
| 98 | Ph | Me | 3-Me-benzyl |
| 99 | Ph | Me | benzyl |
| 100 | Ph | Me | 3,5-F2-benzyl |
| 101 | Ph | Me | 6-Me-2-pyridyl |
| 102 | Ph | Me | —(CH2)2CH(Me)2 |
| 103 | Ph | Me | 4-CF3-2-pyridyl |
| 104 | Ph | Me | 2,5-F2-benzyl |
| 105 | Ph | Me | 2-Cl-benzyl |
| 106 | Ph | Me | 2,4-F2-benzyl |
| 107 | Ph | Me | 4-F-benzyl |
| 108 | Ph | Me | —(CH2)2CH=CH2 |
| 109 | Ph | Me | —CH(Me)CH2CH2Me |
| 110 | 2-F Ph | Me | —CH2CH=CHMe |
| 111 | 2-F Ph | Me | n-Pr |
| 112 | 2-OMe Ph | Me | n-Pr |
| 113 | 2-OMe Ph | Me | —(CH2)2CH=CH2 |
| 114 | Ph | Me | cyclohexyl |
| 115 | Ph | Me | —CH2CH(Me)CH2Me |
| 116 | Ph | Me | —(CH2)2CMe3 |
| 117 | Ph | Me | —CH(CH2Me)2 |
| 118 | Ph | Me | —CH2CMe3 |
| 119 | 2-thienyl | Me | —(CH2)2CH=CH2 |
| 120 | 2-thienyl | Me | cyclopentyl |
| 121 | Ph | Me | —(CH2)3CF3 |
| 122 | Ph | Me | 3-butynyl |
| 123 | Ph | Me | (CH2)2CH(Me)CH2Me |
| 124 | 2-F Ph | Me | cyclopentyl |
| 125 | 2-Cl Ph | Me | cyclopentyl |
| 126 | 2-Me Ph | Me | cyclopentyl |
| 127 | 2-Br Ph | Me | cyclopentyl |
| 128 | 4-F Ph | Me | cyclopentyl |
| 129 | 2-F Ph | Me | 3-butynyl |
| 130 | 2-Cl Ph | Me | 3-butynyl |
| 131 | 2-Me Ph | Me | 3-butynyl |
| 132 | 2-Br Ph | Me | 3-butynyl |
| 133 | 4-F Ph | Me | 3-butynyl |
| 134 | 2-thienyl | Me | 3-butynyl |
| 135 | 2-Cl Ph | Me | n-butyl |
| 136 | 2-Me Ph | Me | n-butyl |
| 137 | 2-Br Ph | Me | n-butyl |
| 138 | 4-F Ph | Me | n-butyl |
| 139 | Ph | Me | cyclopent-1-enyl |
| 140 | Ph | Me | cyclopent-2-enyl |
| 141 | Ph | Me | cyclopropylmethyl |
| 142 | Ph | Me | cyclobutylmethyl |
| 143 | Ph | Me | cyclopentymethyl |
| 144 | Ph | Me | —(CH2)2(3-Cl Ph) |
| 145 | Ph | Me | —(CH2)2(4-OMe Ph) |
| 146 | Ph | Me | —(CH2)2(3,5-Cl2 Ph) |
| 147 | Ph | Me | —(CH2)2(3,5-F2 Ph) |
| 148 | Ph | Me | —(CH2)2(4-F Ph) |
| 149 | Ph | Me | —(CH2)2(2-Me Ph) |
| 150 | Ph | Me | —(CH)2(3-CF3 Ph) |
| 151 | Ph | Me | —(CH2)2(2,5-F2 Ph) |
| 152 | 2-F Ph | Me | —(CH2)2CH=CH2 |
| 153 | 2-Me Ph | Me | —(CH2)2CH=CH2 |
| 154 | 2-Br Ph | Me | —(CH2)2CH=CH2 |
| 155 | 2-Cl Ph | Me | —(CH2)2CH=CH2 |
| 156 | Ph | CH2F | —(CH2)2CH=CH2 |
| 157 | Ph | CH2OMe | —(CH2)2CH=CH2 |
| 158 | Ph | CH2SMe | —(CH2)2CH=CH2 |
| 159 | Ph | CH2N3 | —(CH2)2CH=CH2 |
| 160 | Ph | Me | CH2-cyclopropyl |
| 161 | Ph | Me | CH2-cyclobutyl |
| 162 | Ph | Me | CH2-cyclopentyl |
| 163 | Ph | Me | (CH2)2(4-Cl Ph) |
| 164 | Ph | Me | CH2C(Me)2CH=CH2 |
| 165 | Ph | Me | CH2C(Me)2CH=CH2 |
| 166 | 2-F Ph | Me | CH2-cyclopropyl |
| 167 | 2-F Ph | Me | CH2-cyclobutyl |
| 168 | 2-F Ph | Me | CH2-cyclopentyl |
| 169 | 2-F Ph | Me | (CH2)2(4-Cl Ph) |
| 170 | 2-F Ph | Me | CH2C(Me)2CH=CH2 |
| 171 | 2-F Ph | Me | CH2C(Me)2CH=CH2 |
| 172 | 2-thienyl | Me | CH2-cyclopropyl |
| 173 | 2-thienyl | Me | CH2-cyclobutyl |
| 174 | 2-thienyl | Me | CH2-cyclopentyl |
| 175 | 2-thienyl | Me | (CH2)2(4-Cl Ph) |
| 176 | 2-thienyl | Me | CH2C(Me)2CH=CH2 |
| 177 | 2-thienyl | Me | CH2C(Me)2CH=CH2 |
| 178 | Ph | CH2OMe | CH2-cyclopropyl |
| 179 | Ph | CH2F | CH2-cyclopentyl |
| 180 | Ph | CH2F | Cyclopentyl |

-continued

| Cpd. No. | R¹ | R² | R³ |
|---|---|---|---|
| 181 | Ph | CH2OMe | Cyclopentyl |
| 182 | Ph | CH2OEt | Cyclopentyl |
| 183 | Ph | CH2SMe | Cyclopentyl |
| 184 | Ph | CHF2 | Cyclopentyl |
| 185 | Ph | CH=NOMe | Cyclopentyl |
| 186 | Ph | CH2N3 | Cyclopentyl |
| 187 | 2-F Ph | CH2F | Cyclopentyl |
| 188 | 2-F Ph | CHOMe | Cyclopentyl |
| 189 | 2-F Ph | CH2OEt | Cyclopentyl |
| 190 | 2-F Ph | CHSMe | Cyclopentyl |
| 191 | 2-F Ph | CHF2 | Cyclopentyl |
| 192 | 2-F Ph | CH=NOMe | Cyclopentyl |
| 193 | 2-F Ph | CHN3 | Cyclopentyl |
| 194 | 2-thienyl | CH2F | Cyclopentyl |
| 195 | 2-thienyl | CH2OMe | Cyclopentyl |
| 196 | 2-thienyl | CH2OEt | Cyclopentyl |
| 197 | 2-thienyl | CHSMe | Cyclopentyl |
| 198 | 2-thienyl | CHF2 | Cyclopentyl |
| 199 | 2-thienyl | CH=NOMe | Cyclopentyl |
| 200 | 2-thienyl | CH2N3 | Cyclopentyl |
| 201 | Ph | Me | 3-OMe-5-Cl Ph |
| 202 | 2-F Ph | Me | 3-OMe-5-Cl Ph |
| 203 | 2-thienyl | Me | 3-OMe-5-Cl Ph |
| 204 | 2-Me Ph | Me | 3-OMe-5-Cl Ph |
| 205 | 2-Br Ph | Me | 3-OMe-5-Cl Ph |
| 206 | 2-Cl Ph | Me | 3-OMe-5-Cl Ph |
| 207 | 4-F Ph | Me | 3-OMe-5-Cl Ph |

The numbers 1 to 207 are assigned to these compounds for reference and identification hereafter.

The following compounds of formula (I) are particularly preferred:

2-(2,3-dihydro-6-methyl-4-oxo-5-phenyl-4H-1,3-oxazin-3-yl)-2,4-dimethylpentan-3-one;

2-(2,3-dihydro-6-methyl-4-oxo-5-phenyl-4H-1,3-oxazin-3-yl)-2 methylheptan-3-one;

1-(3,5-difluorophenyl)-2-(2,3-dihydro-6-methyl-4oxo-5-phenyl-4H-1,3-oxazin-3-yl)-2-methylpropan-1-one;

1-(2-fluoro-5-trifluoromethylphenyl)-2-(2,3-dihydro-6-methyl-4-oxo-5-phenyl-4H-1,3-oxazin-3-yl)-2-methylpropan-1-one;

1-(3-chlorophenyl)-3-(2,3-dihydro-6-methyl-4-oxo-5-phenyl-4H-1,3-oxazin-3-yl)-3-methylbutan-2-one;

1-(3-trifluoromethylphenyl)-3-(2,3-dihydro-6-methyl-4-oxo-5-phenyl-4H-1,3-oxazin-3-yl)-3-methylbutan-2-one;

2-(2,3-dihydro-6-methyl-4-oxo-5-phenyl-4H-1,3-oxazin-3-yl)-2-methylhex-5-en-3-one;

4-(2,3-dihydro-6-methyl-4-oxo-5-phenyl-4H-1,3-oxazin-3-yl)-4-methylpent-1-en-3-one;

1-(4-fluorophenyl)-2-[5-2-fluorophenyl)-2,3-dihydro-6-methyl-4-oxo-4H-1,3-oxazin-3-yl]-2-methylpropan-1-one;

4-2,3-dihydro-6-methyl-4-oxo-5-phenyl-4H-1,3-oxazin-3-yl)-4-methylpent-1-yn-3-one;

2-[5-(2-fluorophenyl)2,3-dihydro-6-methyl-4-oxo-4H-1,3-oxazin-3-yl]-1-(2-methylphenyl-2-methylpropan-1-one;

1-(4-fluoro-3-methylphenyl)-2-[5-(2-fluorophenyl)-2,3-dihydro-6-methyl-4-oxo-4H-1,3-oxazin-3-yl]-2-methylpropan-1-one;

2-2,3-dihydro-6methyl-4-oxo-5-phenyl-4H-1,3-oxazin-3-yl)-2-methyl-1-(2-methylphenyl)propan-1-one;

1-(4-fluorophenyl)-2-(2,3-dihydro-6-methyl-4-oxo-5-phenyl-4H-1,3-oxazin-3-yl)-2-methylpropan-1-one;

1-(4-fluoro-3-methylphenyl)-2-(2,3-dihydro-6-methyl-4-oxo-5-phenyl-4H-1,3-oxazin-3-yl)-2-methylpropan-1-one;

2-(2,3-dihydro-6-methyl-4-oxo-5-phenyl-4H-1,3-oxazin-3-yl)-2-methyl-1-phenylpropan-1-one;

1-(2-chlorophenyl)-2-(2,3-dihydro-6-methyl-4-oxo-5-phenyl-4H-1,3-oxazin-3-yl)-2-methylpropan-1-one;

1-(3-chlorophenyl)-2-2,3-dihydro-6-methyl-4-oxo-5-phenyl-4H-1,3-oxazin-3-yl)-2-methylpropan-1-one;

1-(4chlorophenyl)-2-(2,3-dihydro-6-methyl-4-oxo-5-phenyl-4H-1,3-oxazin-3-yl)-2-methylpropan-1-one;

1-(3-trifluoromethylphenyl)-2-(2,3-dihydro-6-methyl-4-oxo-5-phenyl-4H-1,3-oxazin-3-yl)-2-methylpropan-1-one;

1-(3,5-dichlorophenyl)-2-(2,3-dihydro-6-methyl-4-oxo-5-phenyl-4H-1,3-oxazin-3-yl)-2-methylpropan-1-one 3-(2,3-dihydro-6-methyl-4-oxo-5-phenyl-4H-1,3-oxazin-3-yl)-3-methylbutan-2-one;

2-(2,3-dihydro-6-methyl-4-oxo-5-phenyl-4H-1,3-oxazin-3-yl)-2-methylhexan-3-one;

2-(2,3-dihydro-6-methyl-4oxo-5-phenyl-4H-1,3-oxazin-3-yl)-2,5-dimethylhexan-3-one;

2-(2,3-dihydro-6-methyl-4-oxo-5-phenyl-4H-1,3-oxazin-3-yl)-2-methylpentan-3-one;

2-(2,3-dihydro-6-methyl-4-oxo-5-phenyl-4H-1,3-oxazin-3-yl)-2-methylundecan-3-one;

2-(2,3-dihydro-6-methyl-4oxo-5-phenyl-4H-1,3-oxazin-3-yl)-2,4-dimethylhexan-3-one;

1-cyclopropyl-2-(2,3-dihydro-6-methyl-4-oxo-5-phenyl-4H-1,3-oxazin-3-yl)-2-methylpropan-1-one;

2-(2,3-dihydro-6-methyl-4-oxo-5-phenyl-4H-1,3-oxazin-3-yl)-2,4,4-trimethylpentan-3-one;

2-(2,3-dihydro-6-methyl-4-oxo-5-phenyl-4H-1,3-oxazin-3-yl)-2-methyl-1-(2-thienyl)propan-1-one;

2-(2,3-dihydro-6-methyl-4-oxo-5-phenyl-4H-1,3-oxazin-3-yl)-1-(3-furyl)-2-methylpropan-1-one;

1-(2-benzthiazolyl)-2-(2,3-dihydro-6-methyl-4-oxo-5-phenyl-4H-1,3-oxazin-3-yl)-2-methylpropan-1-one;

1-(3,4-dichlorophenyl)-3-(2,3-dihydro-6-methyl-4-oxo-5-phenyl-4H-1,3-oxazin-3-yl)-3-methylbutan-2-one;

1-(3,5-dichlorophenyl)-3-(2,3-dihydro-6-methyl-4-oxo-5-phenyl-4H-1,3-oxazin-3-yl)-3-methylbutan-2-one;

3-(2,3-dihydro-6-methyl-4-oxo-5-phenyl-4H-1,3-oxazin-3-yl)-1-(3,5-dimethylphenyl)-3-methylbutan-2-one;

1-(4-chlorophenyl)-3-(2,3-dihydro-6-methyl-4-oxo-5-phenyl-4H-1,3-oxazin-3-yl)-3-methylbutan-2-one;

1-cyclopentyl-2-(2,3-dihydro-6-methyl-4oxo-5-phenyl-4H-1,3-oxazin-3-yl)-2-methylpropan-1-one;

3-(2,3-dihydro-6-methyl-4-oxo-5-phenyl-4H-1,3-oxazin-3-yl)-3-methyl)-1-(3-methylphenyl)butan-2-one;

2-(2,3-dihydro-6-methyl-4-oxo-5-phenyl-4H-1,3-oxazin-3-yl)-2-methylnonan-3-one;

2-(2,3-dihydro-6-methyl-4-oxo-5-phenyl-4H-1,3-oxazin-3-yl)-2-methyloctan-3-one;

3-(2,3-dihydro-6-methyl-4-oxo-5-phenyl-4H-1,3-oxazin-3-yl)-3-methyl-1-(phenyl)butan-2-one;

1-3,5-difluorophenyl)-3-(2,3-dihydro-6-methyl-4-oxo-5-phenyl-4H-1,3-oxazin-3-yl)-3-methylbutan-2-one;

2-(2,3-diydro-6-methyl-4-oxo-5-phenyl-4H-1,3-oxazin-3-yl)-2-methyl-1-(6-methylpyrid-2-yl)propan-1-one;

2-(2,3-dihydro-6-methyl-4-oxo-5-phenyl-4H-1,3-oxazin-3-yl)-2,6-dimethylheptan-3-one;

2-(2,3-dihydro-6-methyl-4-oxo-5-phenyl-4H-1,3-oxazin-3-yl)-2-methyl-1-(4-trifluoromethylpyrid-2-yl)propan-1-one;

1-(2,5-difluorophenyl)-3-(2,3-dihydro-6-methyl-4-oxo-5-phenyl-4H-1,3-oxazin-3-yl)-3-methylbutan-2-one;

1-(2-chlorophenyl)-3-(2,3-dihydro-6-methyl-4-oxo-5-phenyl-4H-1,3-oxazin-3-yl)-3-methylbutan-2-one;

1-(2,4-difluorophenyl)-3-(2,3-dihydro-6-methyl-4-oxo-5-phenyl-4H-1,3-oxazin-3-yl)-3-methylbutan-2-one;

1-(4-fluorophenyl)-3-(2,3-dihydro-6-methyl-4-oxo-5-phenyl-4H-1,3-oxazin-3-yl)-3-methylbutan-2-one;

2-(2,3-dihydro-6methyl-4oxo-5-phenyl-4H-1,3-oxazin-3-yl)-2-methylhept-6-en-3-one;

2-(2,3-dihydro-6-methyl-4-oxo-5-phenyl-4H-1,3-oxazin-3-yl)-2,4-dimethylheptan-3-one;

2-[2,3-dihydro-5-(2-fluorophenyl)-6-methyl-4-oxo-4H-1,3-oxazin-3-yl]-2-methylheptan-3-one;

2-(2,3-dihydro-6-methyl-4-oxo-5-phenyl-4H-1,3-oxazin-3-yl)-2-methylhept-5-en-3-one;

2-[2,3-dihydro-5-(2-fluorophenyl)-6-methyl-4-oxo-4H-1,3-oxazin-3-yl]-2-methylhexan-3-one;

2-[2,3-dihydro-5-(2-methoxyphenyl)-6-methyl-4-oxo-4H-1,3-oxazin-3-yl]-2-methylhexan-3-one;

2-[2,3-dihydro-5-(2-methoxyphenyl)-6-methyl-4-oxo-4H-1,3-oxazin-3-yl]-2-methylheptan-3-one;

2-[2,3-dihydro-5-2-methoxyphenyl)-6-methyl-4-oxo-4H-1,3-oxazin-3-yl]-2-methylhept-6en-3-one;

1-cyclohexyl-2-(2,3-dihydro-6-methyl-4-oxo-5-phenyl-4H-1,3-oxazin-3-yl)-2-methylpropan-1-one;

2-[2,3-dihydro-6-methyl-4-oxo-5-(2-thienyl)-4H-1,3-oxazin-3-yl]-2-methylhexan-3-one;

2-[2,3-dihydro-6-methyl-4-oxo-5-(2-thienyl)-4H-1,3-oxazin-3-yl]-2-methylheptan-3-one;

2-2,3-dihydro-6-methyl-4-oxo-5-phenyl-4H-1,3-oxazin-3-yl)-2,5-dimethylheptan-3-one;

2-(2,3 -dihydro-6-methyl-4-oxo-5-phenyl-4H-1,3-oxazin-3-yl)-2,6,6-trimethylheptan-3-one;

2-(2,3-dihydro-6-methyl-4-oxo-5-phenyl-4H-1,3-oxazin-3-yl)-4-ethyl-2-methylhexan-3-one;

2-(2,3-dihydro-6-methyl-4-oxo-5-phenyl-4H-1,3-oxazin-3-yl)-2,5,5-trimethylhexan-3-one;

2-[2,3-dihydro-6-methyl-4-oxo-5-(2-thienyl)-4H-1,3-oxazin-3-yl]-2-methylhept-6-en-3-one;

1-cyclopentyl-2-[2,3-dihydro-6-methyl-4-oxo-5-(2-thienyl)-4H-1,3-oxazin-3-yl]-2-methylpropan-1-one;

1-cyclobutyl-2-(2,3-dihydro-6-methyl-4-oxo-5-phenyl-4H-1,3-oxazin-3oxazin-3-yl)-2-methylpropan-1-one;

2-(2,3-dihydro-6-methyl-4oxo-5-phenyl-4H-1,3-oxazin-3-yl)-2-methyl-7,7,7-trifiuoroheptan-3-one;

2-(2,3-dihydro-6-methyl-4-oxo-5-phenyl-4H-1,3-oxazin-3-yl)-2,6-dimethyloctan-3-one; and 2-(2,3-dihydro-6-methyl-4oxo-5-phenyl-4H-1,3-oxazin-3-yl)-2-methylhept-6-yn-3-one.

Compounds of formula (I) above may be prepared by the application or adaptation of known methods (i.e. methods heretofore used or described in the literature). It is to be understood that in the descriptions of the following processes the sequences may be performed in different orders and that suitable protecting groups may be required to achieve the compounds sought.

According to a feature of the present invention compounds of formula (I) wherein Q represents a —C(=O)— group, may be prepared by the oxidation of the corresponding compound of formula (I) wherein Q represents a —CH(OH)— group. The oxidation is generally carried out with a suitable oxidising agent, e.g. chromic acid or pyridinium chlorochromate. The reaction may be performed in a suitable solvent e.g. ether or dichloromethane and at a temperature from 0° C. to the reflux temperature of the solvent.

According to a further feature of the present invention compounds of formula (I) wherein Q represents —CH(OH)— may be prepared by the reaction of an aldehyde of formula (II):

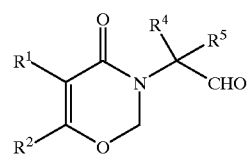

wherein R $^1$, $R^2$, $R^4$ and $R^5$ are as defined above, with an organometallic compound of formula $R^3$—M, wherein $R^3$ is as defined above and M represents a metallic group, preferably a magnesium bromide group or a lithium atom. The reaction is generally performed in an inert solvent e.g. ether or tetrahydrofuran and at a temperature from −78° C. to the reflux temperature of the solvent.

According to a further feature of the present invention compounds of formula (I) wherein Q represents —C(OR$^{11}$)(OR$^{11}$)—, may be prepared by the reaction of a compound of formula (I) wherein Q represents —C(=O)—, with an alcohol of formula $R^{11}$—OH. The reaction is generally performed in the presence of an acid catalyst e.g. 4-toluenesulphonic acid and an inert solvent e.g. toluene and at a temperature from 60° C. to the reflux temperature of the solvent. The reaction is facilitated by removal of the water formed preferably be azeotropic distillation or in the presence of a dehydrating agent e.g. molecular sieve.

Intermediates of formuia (II) may be prepared by the reduction of an ester of formula (III):

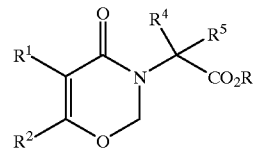

wherein R represents an alkyl group, preferably ethyl. The reaction is generally performed using a suitable reducing agent, e.g. lithium aluminium hydride, in an inert solvent, e.g. tetrahydrofuran, at a temperature from −80° C. to 20° C.

Esters of formula (III) may be prepared by the reaction of a compound of formula (IV):

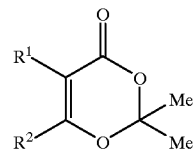

wherein $R^1$ and $R^2$ are as defined above with an imine of formula $CH_2$=N—C($R^4$)($R^5$)$CO_2R$ wherein $R^4$, $R^5$ and R are as defined above. The reaction is generally performed in the presence or absence of solvent and at a temperature from 90° C. to 200° C. or the boiling point of the solvent. The solvent when used is inert, for example xylene, and the acetone produced is preferably removed by distillation.

Compounds of formula (IV) are known or may be prepared by the application or adaptation of known methods.

Compounds of formula (I) above may be prepared by interconversion of other compounds of formula (I) and such conversions constitute further features of the present invention. According to a further feature of the present invention compounds in which n is one or two may be prepared by the oxidation of the sulphur atom of the corresponding compounds in which n is zero or one. The oxidation of the sulphur atom is generally carried out using for example 3-chloroperbenzoic acid in an inert solvent such as dichloromethane at a temperature from −40° C. to room temperature.

Certain compounds of formula (I) can be converted into agriculturally acceptable salts by known methods.

The following non-limiting Examples illustrate the invention. NMR spectra were run in $CDCl_3$ unless otherwise stated.

EXAMPLE 1

A solution of 2-(2,3-dihydro-6-methyl-4-oxo-5-phenyl-4H-1,3-oxazin-3-yl)-2,4-dimethylpentan-3-ol (1.7 g) in dichloromethane was added to a stirred mixture of pyridinium chlorochromate (1.81 g) and powdered molecular sieve (4A) in dichloromethane at 20° C. After 5 hours, ether was added, the mixture filtered through hyflo and evaporated. The residue was purified by dry column chromatography on silica gel, eluting with dichloromethane/ethyl acetate to give 2-(2,3-dihydro-6-methyl-4-oxo-5-phenyl-4H-1,3-oxazin-3-yl)-2,4-dimethylpentan-3-one (Compound 1, 0.84 g) as a white solid, m-p. 98.6–101.6° C.

By proceeding in a similar manner the following compounds were prepared:

2-(2,3-dihydro-6-methyl-4-oxo-5-phenyl-4H-1,3-oxazin-3-yl)-2-methylheptan-3-one (Compound 2, m.p. 75.8–76.6° C.);

1-(3,5-difluorophenyl)-2-(2,3-dihydro-6-methyl-4oxo-5-phenyl-4H-1,3-oxazin-3-yl)-2-methylpropan-1-one (Compound 3), m.p. 156.8–157.8° C.;

3-(2,3-dihydro-6-methyl-4oxo-5-pheny-4H-1,3-oxazin-3-yl)-3-methylbutan-2-one (Compound 27, m.p. 118–119° C.);

2-(2,3-dihydro-6-methyl-4-oxo-5-phenyl-4H-1,3-oxazin-3-yl)-2-methylhexan-3-one (Compound 29, m.p. 118–119° C.;

2-(2,3-dihydro-6-methyl-4-oxo-5-phenyl-4H-1,3-oxazin-3-yl)-2,5-dimethylhexan-3-one (Compound 30, m.p. 72–73° C.);

2-(2,3-dihydro-6-methyl-4-oxo-5-phenyl-4H-1,3-oxazin-3-yl)-2-methylpentan-3-one (Compound 28, m.p. 102–103° C.);

2-(2,3-dihydro-6-methyl-4oxo-5-phenyl-4H-1,3-oxazin-3-yl)-2-methylundecan-3-one (Compound 38), NMR 0.8(t, 3H), 1.2(m, 10H), 1.4(s,6H), 1.6(q,2H), 1.85(s,3H), 2.4(t, 2H), 5.15(s,2H), 7.25(m,5H);

2-(2,3-dihydro-6-methyl-4oxo-5-phenyl-4H-1,3-oxazin-3-yl)-2,4-dimethylhexan-3-one (Compound 32; m.p. 84–84.5° C.);

1-cyclopropyl-2-(2,3-dihydro-6-methyl-4-oxo-5-phenyl-4H-1,3-oxazin-3-yl)-2-methylpropan-1-one (Compound 31, m.p. 126–128° C.);

2-(2,3-dihydro-6-methyl-4-oxo-5-phenyl-4H-1,3-oxazin-3-yl)-2,4,4-trimethylpentan-3-one (Compound 90, m.p. 139–140.5° C.);

2-(2,3-dihydro-6-methyl-4-oxo-5-phenyl-4H-1,3-oxazin-3-yl)-2-methyl-1-(2-thienyl)propan-1-one (Compound 91, m.p. 152–153.5° C.);

2-(2,3-dihydro-6-methyl-4oxo-5-phenyl-4H-1,3-oxazin-3-yl)-1-(3-furyl)-2-methylpropan-1-one (Compound 92, m.p. 164–165° C.);

1-(2-benzthiazolyl)-2-(2,3-dihydro-6-methyl-4-oxo-5-phenyl-4H-1,3-oxazin-3-yl)-2-methylpropan-1-one (Compound 93, m.p. 169–169.5° C.);

1-(3,4-dichlorophenyl)-3-(2.3-dihydro-6-methyl-4-oxo-5-phenyl-4H-1,3-oxazin-3-yl)-3-methylbutan-2-one (Compound 94, m.p. 120–121° C.);

1-(3,5-dichlorophenyl)-3-(2,3-dihydro-6-methyl-4-oxo-5-phenyl-4H-1,3-oxazin-3-yl)-3-methylbutan-2-one (Compound 39, m.p. 120.5–121.5° C.);

3-(2,3-dihydro-6-methyl-4oxo-5-phenyl-4H-1,3-oxazin-3-yl)-1-(3,5-dimethylphenyl)-3-methylbutan-2-one (Compound 95, m.p. 119–120° C.);

1-(4-chlorophenyl)-3-(2,3-dihydro-6-methyl-4-oxo-5-phenyl-4H-1,3-oxazin-3-yl)-3-methylbutan-2-one (Compound 96, m.p. 165.5–166° C.);

1-cyclopentyl-2-(2,3-dihydro-6-methyl-4-oxo-5-phenyl-4H-1,3-oxazin-3-yl)-2-methylpropan-1-one (Compound 97, m.p. 126–128° C.);

3-2,3-dihydro-6-methyl-4-oxo-5-phenyl-4H-1,3-oxazin-3-yl)-3-methyl)-1-(3-methylphenyl)butan-2-one (Compound 98, m.p. 97.5–99° C.);

2-(2,3-dihydro-6-methyl-4-oxo-5-phenyl-4H-1,3-oxazin-3-yl)-2-methylnonan-3-one (Compound 35, m.p. 59–60° C.);

2-(2,3-dihydro-6-methyl-4-oxo-5-phenyl-4H-1,3-oxazin-3-yl)-2-methyloctan-3-one (Compound 34, m.p. 82–82.5° C.);

3-(2,3-dihydro-6-methyl-4-oxo-5-phenyl-4H-1,3-oxazin-3-yl)-3-methyl-1-(phenyl)butan-2-one (Compound 99, m.p. 117–118° C.);

1-(3,5-difluorophenyl)-3-(2,3-dihydro-6-methyl-4-oxo-5-phenyl-4H-1,3-oxazin-3-yl)-3-methylbutan-2-one (Compound 100, m-p. 92.5–94° C.);

2-(2,3-dihydro-6-methyl-4-oxo-5-phenyl-4H-1,3-oxazin-3-yl)-2-methyl-1-(6-methylpyrid-2-yl)propan-1-one (Compound 101, m.p. 76.5–77.5° C.;

2-(2,3-dihydro-6-methyl-4-oxo-5-phenyl-4H-1,3-oxazin-3-yl)-2,6-dimethylheptan-3-one (Compound 102, m.p. 83.5–84° C.);

2-(2,3-dihydro-6-methyl-4-oxo-5-phenyl-4H-1,3-oxazin-3-yl)-2-methyl-1-(4-trifluoromethylpyrid-2-yl)propan-1-one (Compound 103, m.p. 134–135° C.);

1-(2,5-difluorophenyl)-3-(2,3-dihydro-6-methyl-4-oxo-5-phenyl-4H-1,3-oxazin-3-yl)-3-methylbutan-2-one (Compound 104, m.p. 98–99° C.);

1-(2-chlorophenyl)-3-(2,3-dihydro-6-methyl-4-oxo-5-phenyl-4H-1,3-oxazin-3-yl)-3-methylbutan-2-one (Compound 105, m.p. 140.5–141° C.);

1-(2,4-difluorophenyl)-3-(2,3-dihydro-6-methyl-4-oxo-5-phenyl-4H-1,3-oxazin-3-yl)-3-methylbutan-2-one (Compound 106, m.p. 135–136° C.);

1-(4-fluorophenyl)-3-(2,3-dihydro-6-methyl-4-oxo-5-phenyl-4H-1,3-oxazin-3-yl)-3-methylbutan-2-one (Compound 107, m.p. 118–119° C.);

2-(2,3-dihydro-6-methyl-4-oxo-5-phenyl-4H-1,3-oxazin-3-yl)-2-methylhept-6-en-3-one (Compound 108, m.p. 91–92° C.);

2-(2,3-dihydro-6-methyl-4-oxo-5-phenyl-4H-1,3-oxazin-3-yl)-2,4-dimethylheptan-3-one (Compound 109), NMR 0.7 (t,3H), 1.0(d,3H), 1.15–1.3(m,4H), 1.45(s,6H), 1.85(s,3H), 2.9(m,1H), 5.2(s,2H), 7.25(m,5H);

2-[2,3-dihydro-5-(2-fluorophenyl)-6-methyl-4-oxo-4H-1, 3-oxazin-3-yl]-2-methylheptan-3-one (Compound 43), NMR 0.9(t,3H), 1.25(m,2H), 1.45(s,6H), 1.6(q,2H), 1.9(s, 3H), 2.5(t,2H), 5.3(s,2H), 7.1(m,2H), 7.3(m,2H);

2-(2,3-dihydro-6-methyl-4-oxo-5-phenyl-4H-1,3-oxazin-3-yl)-2-methylhept-5-en-3-one (Compound 110), NMR 1.15 (d,3H), 1.2(s,6H), 1.85(s,3H), 5.0(q,1H), 5.2(s,2H), 5.7(q, 1H), 7.25(m,5H);

2-[2,3-dihydro-5-(2-fluorophenyl)-6-methyl-4-oxo-4H-1,3-oxazin-3-yl]-2-methylhexan-3-one (Compound 111), NMR 0.8(t,3H), 1.4(s,6H), 1.6(m,2H), 1.8(s,3H), 2.4(t,2H), 5.2(s,2H), 7.05(m,2H), 7.25(m,2H);

2-[2,3-dihydro-5-(2-methoxyphenyl)-6-methyl-4-oxo-4H-1,3-oxazin-3-yl]-2-methylhexan-3-one (Compound 112, m.p. 87–88.5° C.);

2-[2,3-dihydro-5-(2-methoxyphenyl)-6-methyl-4-oxo-4H-1,3-oxazin-3-yl]-2-methylheptan-3-one (Compound 48, mp. 65–67° C.);

2-[2,3-dihydro-5-(2-methoxyphenyl)-6-methyl-4-oxo-4H-1,3-oxazin-3-yl]-2-methylhept-6-en-3-one (Compound 113, m.p. 62–63° C.);

1-cyclohexyl-2-(2,3-dihydro-6-methyl-4-oxo-5-phenyl-4H-1,3-oxazin-3-yl)-2-methylpropan-1-one (Compound 36, m.p. 94–96° C.);

2-[2,3-dihydro-6-methyl-4-oxo-5-2-thienyl)-4H-1,3-oxazin-3-yl]-2-methylhexan-3-one (Compound 114, m.p. 94° C.;

2-[2,3-dihydro-6-methyl-4-oxo-5-(2-thienyl)-4H-1,3-oxazin-3-yl]-2-methylheptan-3-one (Compound 56, m.p. 75–76° C.);

2-2,3-dihydro-6-methyl-4-oxo-5-phenyl-4H-1,3-oxazin-3yl)-2,5-dimethylheptan-3-one (Compound 115, m.p. 55–56° C.);

2-(2,3-dihydro-6-methyl-4-oxo-5-phenyl-4H-1,3-oxazin-3-yl)-2,6,6-trimethylheptan-3-one (Compound 116, m.p. 107.5–109° C.);

2-(2,3-dihydro-6-methyl-4-oxo-5-phenyl-4H-1,3-oxazin-3-yl)-4-ethyl-2-methylhexan-3-one (Compound 117) NMR 0.77 (t,3H), 1.4(m,2H), 1.5(s,6H), 1.6–1.7(m,2H), 1.8(s, 3H), 2.65(m,1H), 5.2(s,2H), 7.1–7.3(m,5H);

2-(2,3-dihydro-6-methyl-4-oxo-5-phenyl-4H-1,3-oxazin-3-yl)-2,5,5-trimethylhexan-3-one (Compound 118), NMR 0.92(s,9H), 1.33(s,6H), 2.1 (s,3H), 2.4(s,2H), 5.2(s,2H), 7.15–7.3(m,5H);

2-[2,3-dihydro-6-methyl-4-oxo-5-(2-thienyl)-4H-1,3-oxazin-3-yl]-2-methylhept-6-en-3-one (Compound 119, m.p. 79–81° C.);

1-cyclopentyl-2-[2,3-dihydro-6-methyl-4-oxo-5-(2-thienyl)-4H-1,3-oxazin-3-yl]-2-methylpropan-1-one (Compound 120, m.p. 103–104.5° C.);

1-cyclobutyl-2-(2,3-dihydro-6-methyl-4-oxo-5-phenyl-4H-1,3-oxazin-3-yl)-2-methylpropan-1-one (Compound 33, m.p. 136–137.5° C.); and 2-(2,3-dihydro-6-methyl-4-oxo-5-phenyl-4H-1,3-oxazin-3-yl)-2-methyl-7,7,7-trifluoroheptan-3-one (Compound 121, mp. 83–84.5° C.).

The same procedure was employed but with the exclusion of molecular sieve to prepare the following compounds:

1-(2-fluoro-5-trifluoromethylphenyl)-2-(2,3-dihydro-6-methyl-4-oxo-5-phenyl-4H-1,3-oxazin-3-yl)-2-methylpropan-1-one (Compound 4), m.p. 113–114.6° C.;

1-(3-chlorophenyl)-3-(2,3-dihydro-6-methyl-4-oxo-5-phenyl-4H-1,3-oxazin-3-yl)-3-methylbutan-2-one (Compound 5), m.p. 134.5–136° C.; and 1-(3-trifluoromethylphenyl)-3-(2,3-dihydro-6-methyl-4-oxo-5-phenyl-4H-1,3-oxazin-3-yl)-3-methylbutan-2-one (Compound 6), m.p. 105.9–106.9° C.;

EXAMPLE 2

Chromic acid [1.7 ml of a solution prepared by the addition of a solution of sodium dichromate (0.4 g) in water (1.2 ml) to concentrated sulphuric acid (0.54 ml) and diluted to 2 ml with water] was added dropwise at 25° C. to a stirred solution of 2-(2,3-dihydro-6-methyl-4-oxo-5-phenyl-4H-1, 3-oxazin-3-yl)-2-methylhex-5-ene-3-ol (1.0 g) in ether. After 18 hours the ether layer was separated, washed with sodium bicarbonate solution (2N) and with brine, dried (magnesium sulphate) and evaporated. The residue was purified by dry column chromatography on silica gel eluting with dichloromethane, to give 2-(2,3-dihydro-6-methyl-4-oxo-5-phenyl-4H-1,3-oxazin-3-yl)-2-methylhex-5-en-3-one (Compound 7, 0.12 g) as a yellow oil, NMR $^1$H δ1.4(s,6H), 1.88(s,3H), 3.22(d,2H), 5.05(m,2H), 5.22(s,2H), 5.9(m.1H), 7.2–7.35(m,5H).

By proceeding in a similar manner, the following compounds of formula (I) were prepared:

4-(2,3-dihydro-6-methyl-4-oxo-5-phenyl-4H-1,3-oxazin-3-yl)-4-methylpent-1-en-3-one (Compound 8) m.p. 123–124° C., 1-(4fluorophenyl)-2-[5-(2-fluorophenyl)-2,3-dihydro-6-methyl-4-oxo-4H-1,3-oxazin-3-yl]-2-methylpropan-1-one (Compound 9), m.p. 92–96° C.;

4-(2,3-dihydro-6-methyl-4-oxo-5-phenyl-4H-1,3-oxazin-3-yl)-4-methylpent-1-yn-3-one (Compound 10) as a yellow oil, NMR $^1$H δ1.45(s,6H), 1.9(s,3H), 3.05(s,1H), 5.25(s,2H), 7.2–7.4(m,5H);

2-[5-(2-fluorophenyl)-2,3-dihydro-6-methyl-4-oxo-4H-1, 3-oxazin-3-yl]-1-(2-methylphenyl)-2-methylpropan-1-one (Compound 11) as a colourless gum, NMR $^1$H δ1.7(s,6H), 1.85(s,3H), 2.39(s,3H), 5.4(s,2H), 6.9–7.7(m,8H);

1-(4-fluoro-3-methylphenyl)-2-[5-(2-fluorophenyl)-2,3-dihydro-6-methyl-4-oxo-4H-1,3-oxazin-3-yl]-2-methylpropan-1-one (Compound 12) as a yellow oil, NMR $^1$H δ1.6(s,6H), 1.85(s,3H), 2.2(s,3H), 5.4(s,2H), 6.85–7.9 (m,7H);

2-(2,3-dihydro-6-methyl-4-oxo-5-phenyl-4H-1,3-oxazin-3-yl)-2-methyl-1-(2-methylphenyl)propan-1-one (Compound 13) as a colourless oil, NMR $^1$H δ1.6(s,6H), 1.85(s,3H), 2.35(s,3H), 5.3(s,2H), 6.9(dd,2H), 7.05(t,1H), 7.1–7.3(m,5H), 7.55(d,1H);

1-(4-fluorophenyl)-2-2,3-dihydro-6-methyl-4-oxo-5-phenyl-4H-1,3-oxazin-3-yl)-2-methylpropan-1-one (Compound 14) as a yellow solid, NMR $^1$H δ1.55(s,6H), 1.85(s,3H), 5.35(s,2H), 6.9–7.05(m,4H), 7.15–7.25(m,3H), 8.0(dd,2H); and 1-(4fluoro-3-methylphenyl)-2-(2,3-dihydro-6-methyl-4-oxo-5-phenyl-4H-1,3-oxazin-3-yl)-2-methylpropan-1-one (Compound 15) as a cream solid, NMR $^1$H δ1.55(s,6H), 1.85(s,3H), 2.2(d,3H), 5.35(s,2H), 6.9(m,3H), 7.1–7.3(m, 3H), 7.75–7.9(m,2H).

EXAMPLE 3

Oxalyl chloride (1.05 g) was added to a stirred mixture of dimethylsulphoxide (1.3 g) in dichloromethane at –60° C. After 10 minutes, 2-(2,3-dihydro-6-methyl-4-oxo-5-phenyl-4H-1,3-oxazin-3yl)-2-methyl-1-phenylpropan-1-ol (1.86 g) was added, followed after 0.5 hour by triethylamine (2.8 g). The mixture was warmed to room temperature, poured onto water and the organic phase washed with water, dried (magnesium sulphate) and evaporated to give, after purification by column chromatography on silica gel and eluting with hexane/ethyl acetate (5:1), 2-(2,3-dihydro-6-methyl-4-oxo-5-phenyl-4H-1,3-oxazin-3-yl)-2-methyl-1-phenylpropan-1-one (Compound 16, m.p. 122–123° C.).

By proceeding in a similar manner the following compounds of formula (I) were prepared:

1-(2-chlorophenyl)-2-(2,3-dihydro-6-methyl-4-oxo-5-phenyl-4H-1,3-oxazin-3-yl)-2-methylpropan-1-one (Compound 17, m.p. 142–145° C.);

1-(3-chlorophenyl)-2-(2,3-dihydro-6-methyl-4-oxo-5-phenyl-4H-1,3-oxazin-3-yl)-2-methylpropan-1-one (Compound 18, m.p. 134–136° C.);

1-(4-chlorophenyl)-2-(2,3-dihydro-6-methyl-4-oxo-5-phenyl-4H-1,3-oxazin-3-yl)-2-methylpropan-1-one (Compound 19, m.p. 131–132° C.);

1-(3-trifluoromethylphenyl)-2-(2,3-dihydro-6-methyl-4-oxo-5-phenyl-4H-1,3-oxazin-3-yl)-2-methylpropan-1-one (Compound 20, m.p. 108–109° C.); and 1-(3,5-dichlorophenyl)-2-(2,3-dihydro-6-methyl-4-oxo-5-phenyl-4H-1,3-oxazin-3-yl)-2-methylpropan-1-one (Compound 21, m.p. 164–167° C.).

EXAMPLE 4

Isopropylmagnesium chloride (5 ml of a 2M solution in tetrahydrofuran) was added during 10 minutes to a stirred solution of 2-(2,3-dihydro-6-methyl-4-oxo-5-phenyl-4H-1,3-oxazin-3-yl)-2-methylpropionaldehyde (2 g) in tetrahydrofuran at 0° C. under an inert atmosphere. The mixture was allowed to warm to 10° C. over 1 hour, poured onto saturated ammonium chloride solution and extracted (ether). The organic phase was dried (magnesium sulphate) and evaporated to give 2-(2,3-dihydro-6-methyl-4-oxo-5-phenyl-4H-1,3-oxazin-3-yl)-2,4-dimethylpentan-3-ol (2.26 g) as a yellow gum, m.p. 42–54° C., NMR $^1$H δ0.85(d,3H), 0.95(d,3H), 1.4(s,3H), 1.5(s,3H), 1.65(m,1H), 1.85(s,3H), 3.25(dd,1H), 5.0(d,1H), 5.1(d,1H), 5.25(d,1H), 7.15–7.35 (m,5H).

By proceeding in a similar manner the following compounds of formula (I) were prepared:

2-(2,3-dihydro-6-methyl-4-oxo-5-phenyl-4H-1,3-oxazin-3-yl)-2-methylheptan-3-ol as an off white solid, m.p. 76–84° C.;

2-(2,3-dihydro-6-methyl-4-oxo-5-phenyl-4H-1,3-oxazin-3-yl)-2-methylhex-5-en-3-ol as an oil, NMR $^1$H δ1.35(s, 3H), 1.49(s,3H), 1.88(s,3H), 1.9–2.2(m,2H), 3.65(dt,1H), 4.55(d,1H), 5.0(m,2H), 5.1(d,1H), 5.2(d,1H), 5.85(m,1H), 7.15–7.35(m,5H);

4-(2,3-dihydro-6-methyl-4-oxo-5-phenyl-4H-1,3-oxazin-3-yl)-4-methylpent-1-en-3-ol as a yellow oil, NMR $^1$H δ1.35 (s,3H), 1.5(s,3H), 1.85(s,3H), 4.05(m,1H), 5.0(d,1H), 5.1–5.29(m,4H), 5.75(ddd,1H), 7.15–7.3(m,5H);

1-(4-fluorophenyl)-2-[5-(2-fluorophenyl)-2,3-dihydro-6-methyl-4-oxo-4H-1,3-oxazin-3-yl]-2-methylpropan-1-ol as a colourless oil, NMR 1.52(s,6H), 1.8(s,3H), 4.45(brs,1H), 4.75(s,2H), 4.8(s,1H), 6.9–7.4(m,8H);

4-(2,3-dihydro-6-methyl-4-oxo-5-phenyl-4H-1,3-oxazin-3-yl)-4-methylpent-1-yn-3-ol as a yellow oil NMR $^1$H δ1.5 (s,3H), 1.55(s,3H), 1.85(s,3H), 2.35(s,1H), 4.35(dd,1H), 5.15(d,1H), 5.30(d,1H), 5.85(d,1H), 7.15–7.35(m,5H);

2-[5-(2-fluorophenyl)-2,3-dihydro-6-methyl-4-oxo-4H-1,3-oxazin-3-yl]-1-(2-methylphenyl)-2-methylpropan-1-ol as a pale yellow oil, NMR $^1$H δ1.4(s,3H), 1.65(s,3H), 1.8(s, 3H), 2.3(s,3H), 4.7(d,1H), 4.88(d,1H), 5.1(d,1H), 7.74(m 8H);

1-(4fluoro-3-methylphenyl)-2-[5-(2-fluorophenyl)-2,3-dihydro-6-methyl-4oxo-4H-1,3-oxazin-3-yl]-2-methylpropan-1-ol as a colourless oil NMR $^1$H δ1.3(s,3H), 1.6(s,3H), 1.8(s,3H), 2.2(s,3H), 4.65(brs,1H), 4.75(s,1H), 5.15(s,2H), 6.8–7.4(m,7H);

1-(3,5-difluorophenyl)-2-(2,3-dihydro-6-methyl-4-oxo-5-phenyl-4H-1,3-oxazin-3-yl)-2-methylpropan-1-ol as a white solid, m.p. 87.6–89° C.;

1-(2-fluoro-5-trifluoromethylphenyl)-2-(2,3-dihydro-6-methyl-4-oxo-5-phenyl-4H-1,3 -oxazin-3-yl)-2-methylpropan-1-ol NMR $^1$H δ1.4(s,3H), 1.75(s,3H), 1.9(s, 3H), 4.55(d,1H), 4.9(d,1H), 5.1(d,1H), 6.98(d,1H), 7.12(t, 1H), 7.28(dd,2H), 7.35–7.48(m,3H), 7.5–7.6(m,1H), 7.7–7.8(m,1H);

1-(3-chlorophenyl)-3-(2,3-dihydro-6-methyl-4-oxo-5-phenyl-4H-1,3-oxazin-3-yl)-3-methylbutan-2-ol as a white solid, m.p. 116.9–118.1° C.;

1-(3-trifluoromethylphenyl)-3-(2,3-dihydro-6-methyl-4-oxo-5-phenyl-4H-1,3-oxazin-3-yl)3-methylbutan-2-ol as a white solid, m.p. 67–68.2° C.;

2-(2,3-dihydro-6-methyl-4-oxo-5-phenyl-4H-1,3-oxazin-3-yl)-2-methyl-1-(2-methylphenyl)propan-1-ol as a white solid, NMR $^1$H δ1.3(s,3H), 1.55(s,3H), 1.7(s,3H), 2.3(s,3H), 4.7(d,1H), 4.88(d,1H), 5.1(d,1H), 5.55(d,1H), 7.0–7.4(m, 9H);

1-(4-fluorophenyl)-2-(2,3-dihydro-6-methyl-4-oxo-5-phenyl-4H-1,3-oxazin-3-yl)-2-methylpropan-1-ol as a colourless oil NMR $^1$H δ1.4(s,3H), 1.68(s,3H), 1.9(s,3H), 4.5(d,1H), 4.75(d,1H), 4.8(d,1H), 5.9(d,1H), 7.0(t,2H), 7.2–7.45(m,7H);

1-(4-fluoro-3-methylphenyl)-2-(2,3-dihydro-6-methyl-4-oxo-5-phenyl-4H-1,3-oxazin-3-yl)-2-methylpropan-1-ol as a colourless oil NMR $^1$H δ1.35(s,3H), 1.6(s,3H), 1.7(s,3H), 2.2(s,3H), 4.45(d,1H), 4.68(d,1H), 4.75(d,1H), 5.78(d,1H), 6.88(t,1H), 6.95–7.05(m,2H), 7.2–7.4(m,5H);

2-(2,3-dihydro-6-methyl-4-oxo-5-phenyl-4H-1,3-oxazin-3-yl)-2-methyl-1-phenylpropan-1-ol, m.p. 150–154° C.;

1-(2-chlorophenyl)-2-(2,3-dihydro-6-methyl-4-oxo-5-phenyl-4H-1,3-oxazin-3-yl)-2-methylpropan-1-ol, m.p. 141–143° C.;

1-(3-chlorophenyl)-2-(2,3-dihydro-6-methyl-4-oxo-5-phenyl-4H-1,3-oxazin-3-yl)-2-methylpropan-1-ol, m.p. 97–98° C.;

1-(4-chlorophenyl)-2-(2,3-dihydro-6-methyl-4-oxo-5-phenyl-4H-1,3-oxazin-3-yl)-2-methylpropan-1-ol, m.p. 138–139° C.;

1-(3-trifluoromethylphenyl)-2-(2,3-dihydro-6-methyl-4-oxo-5-phenyl-4H-1,3-oxazin-3-yl)-2-methylpropan-1-ol, m.p. 107–108° C., and 1-(3,5-dichlorophenyl)-2-(2,3-dihydro-6-methyl-4-oxo-5-phenyl-4H-1,3-oxazin-3-yl)-2-methylpropan-1-ol, m.p. 141–144° C.

By proceeding in a similar manner the following compounds of formula (I) in which Q is —CH(OH)— were also prepared. In the table that follows 'Ph' means phenyl, 'Me' means methyl, 'Et' means ethyl 'Pr' means propyl and 'Bu' means butyl. Where subscripts are omitted they are intended, for example CH=CH2 means $CH=CH_2$.

| R1 | R2 | R3 | R4 | R5 | m.p. (° C.) or NMR |
|---|---|---|---|---|---|
| Ph | Me | Me | Me | Me | a |
| Ph | Me | n-Pr | Me | Me | 82.5–83.5 |
| Ph | Me | —CH2CHMe2 | Me | Me | 91–92 |
| Ph | Me | Et | Me | Me | 93–95 |
| Ph | Me | n-octyl | Me | Me | 64.5–67 |
| Ph | Me | —CH(Me)CH2Me | Me | Me | b |

-continued

| R1 | R2 | R3 | R4 | R5 | m.p. (° C.) or NMR |
|---|---|---|---|---|---|
| Ph | Me | cyclopropyl | Me | Me | 64–64.5 |
| Ph | Me | t-Bu | Me | Me | 122–123 |
| Ph | Me | 3,4-Cl2 benzyl | Me | Me | 112–113 |
| Ph | Me | 3,5-Cl2 benzyl | Me | Me | 100.5–101.5 |
| Ph | Me | 3,5-Me2 benzyl | Me | Me | 108–109 |
| Ph | Me | 4-Cl benzyl | Me | Me | 91.5–92.5 |
| Ph | Me | cyclopentyl | Me | Me | 89.5–90 |
| Ph | Me | 3-Me benzyl | Me | Me | 108.5–109.5 |
| Ph | Me | n-hexyl | Me | Me | 77.5–79 |
| Ph | Me | n-pentyl | Me | Me | 78.5–79.5 |
| Ph | Me | benzyl | Me | Me | 142–143 |
| Ph | Me | 3,5-F2 benzyl | Me | Me | 129–130.5 |
| Ph | Me | —(CH2)2CHMe2 | Me | Me | 112–112.5 |
| Ph | Me | 2,5-F2 benzyl | Me | Me | 113–114 |
| Ph | Me | 2-Cl benzyl | Me | Me | 94–95.5 |
| Ph | Me | 2,4-F2 benzyl | Me | Me | 105.5–106.5 |
| Ph | Me | 4-F benzyl | Me | Me | 76–78 |
| Ph | Me | —(CH2)2CH=CH2 | Me | Me | 74–75 |
| Ph | Me | —CH(Me)CH2CH2Me | Me | Me | 88.5–90 |
| 2-F Ph | Me | n-Bu | Me | Me | 84.5–86 |
| Ph | Me | —CH2CH=CHMe | Me | Me | |
| 2-F Ph | Me | n-Pr | Me | Me | c |
| 2-OMe—Ph | Me | n-Pr | Me | Me | d |
| 2-OMe—Ph | Me | n-Bu | Me | Me | e |
| 2-OMe—Ph | Me | —(CH2)2CH=CH2 | Me | Me | f |
| Ph | Me | cyclohexyl | Me | Me | 58.5–60 |
| 2-thienyl | Me | n-Pr | Me | Me | 88–89 |
| 2-thienyl | Me | n-Bu | Me | Me | 98.5–99 |
| Ph | Me | —CH2CH(Me)CH2Me | Me | Me | g |
| Ph | Me | —(CH2)2CMe3 | Me | Me | |
| Ph | Me | —CH(CH2Me)CH2Me | Me | Me | |
| Ph | Me | —CH2CMe3 | Me | Me | |
| 2-thienyl | Me | —(CH2)2CH=CH2 | Me | Me | 66–69 |
| 2-thienyl | Me | cyclopentyl | Me | Me | 81–83 |
| Ph | Me | cyclobutyl | Me | Me | 109.5–110 |
| Ph | Me | —(CH2)3CF3 | Me | Me | 91–92 |

1-H NMR (ppm):

(a) 1.1(d,3H), 1.4(s,3H), 1.53(s,3H), 1.9(s,3H), 3.82(q, 1H), 5.09(d1H), 5.15 and 5.28(dd,2H), 7.2–7.4(m,5H)

(b) 0.95(m,6H), 1.3(m,3H), 1.4(d,3H), 1.6(d,3H), 1.9(s, 3H), 3.4(q,1H), 5.0(q,1H), 5.15(d,1H), 5.35(d,1H), 7.35(m, 5H)

(c) 0.9(t,3H), 1.2(m,2H), 1.35(s,3H), 1.5(s,3H), 1.6(m, 2H), 1.9(s,3H), 3.5(t,1H), 4.6(d,1H), 5.1(d,1H), 5.3(d,1H), 7.0–7.3(m,5H)

(d) 1.3(s,6H), 1.5(m,2H), 1.9(m,3H), 3.78(s,3H), 4.9–5.2 (m,2H), 5.24(s,2H), 6.95(m,2H), 7.25(m,2H)

(e) 0.8(m,3H), 1.12(t,3H), 1.1–1.5(m,2H), 1.8(m,3H), 3.4 (q,2H), 3.7(s,3H), 4.85(br,1H), 5.1(m,1H), 5.2(m,1H), 6.9 (m,2H), 7.2(m,2H)

(f) 1.4(s,6H), 1.88(s,3H), 2.35(m,2H), 2.6(m,2H), 3.75(s, 3H), 5.0(m,2H), 5.27(s,2H), 5.75–5.9(m,1H), 6.9(m,2H), 7.17(m,1H), 7.25(m,1H), 9.4(s,1H)

(g) 0.9(t,1H), 0.9(d,3H), 1.0–1.3(m,4H), 1.4(s,3H), 1.55 (s,3H), 1.7(m,1H), 1.9(s,3H), 3.6(d,1H), 5.1(d,1H), 5.3(d, 1H), 7.2–7.4(m,5H).

EXAMPLE 5

A solution of sec-butylmagnesium chloride (1.14 ml of a 2M solution in tetrahydrofuran) was added to a stirred solution of 4-2,3-dihydro-6-methyl-4-oxo-5-phenyl-4H-1,3-oxazin-3-yl)-4-methylpent-1-en-3-one (0.5 g) in tetrahydrofuran kept below 0° C. under an inert atmosphere. After 2 hours ethyl acetate and ammonium chloride solution were added and the organic phase washed (brine) and evaporated to give 2-(2,3-dihydro-6-methyl-4-oxo-5-phenyl-4H-1,3-oxazin-3-yl)-2,6-dimethyloctan-3-one (Compound 122, 0.48 g), NMR 1.55(s,3H), 1.6(s,3H), 2.1(s,3H), 2.5(s,1H), 5.2(m,3H), 5.6(d,1H), 5.8(q,1H), 7.25(m,5H).

By proceeding in a similar manner the following compound was obtained:

2-(2,3-dihydro-6-methyl-4-oxo-5-phenyl-4H-1,3-oxazin-3-yl)-2-methylhept-6-yn-3-one (Compound 123), NMR 0.9 (d,3H), 0.9(t,3H), 1.2(m,5H), 1.45(s,6H), 1.9(s,3H), 2.5(m, 2H), 5.3(s,2H), 7.3(m,5H).

EXAMPLE 6

2-Thienyl lithium (4.25 ml) of a 1M solution in tetrahydrofuran) was added during 5 minutes to a solution of 2-(2,3-dihydro-6-methyl-4-oxo-5-phenyl-4H-1,3-oxazin-3-yl)-2-methylpropionaldehyde (1.0 g) in tetrahydrofuran whilst stirring at room temperature under an inert atmosphere. After 72 hours hydrochloric acid (2M) and ethyl acetate were added, the organic phase dried (MgSO4) and evaporated. The residue was purified by chromatography on silica gel eluting with hexane/ethyl acetate (3:1) to give, after trituration with hexane, 2-2,3-dihydro-6-methyl-4oxo-5-phenyl-4H-1,3-oxazin-3-yl)-2-methyl-1-2-thienyl) propan-1-ol (0.36 g), m.p. 149–151° C.

By proceeding in a similar manner the following compounds were also obtained:

2-(2,3-dihydro-6-methyl-4-oxo-5-phenyl-4H-1,3-oxazin-3-yl)-1-(3-furyl)-2-methylpropan-1-ol, m.p. 132–132.5° C.;

2-(2,3-dihydro-6-methyl-4-oxo-5-phenyl-4H-1,3-oxazin-3-yl)-2-methyl-1-(6-methyl-2-pyridyl)propan-1-ol, NMR 1.6(s,6H), 1.9(s,3H), 2.5(s,3H), 4.75(d,1H), 5.0(d,1H), 5.1 (d,1H), 5.65(d,1H), 7.05(d,1H), 7.15(d,1H), 7.2–7.4(m,5H), 7.55(t,1H); and 2-(2,3-dihydro-6-methyl-4-oxo-5-phenyl-4H-1,3-oxazin-3-yl)-2-methyl-1-(4-trifluoromethyl-2-pyridyl)propan-1-ol, NMR 1.6(s,3H), 1.6(s,3H), 1.85(s,3H), 4.5(d,1H), 4.95(d, 1H), 5.1(d,1H), 6.2(d,1H), 7.1(d,1H), 7.2–7.4(m,5H), 7.7(s, 1H), 8.7(d,1H).

REFERENCE EXAMPLE 1

A solution of ethyl 2-(2,3-dihydro-6-methyl-4-oxo-5-phenyyl-4H-1,3-oxazin-3-yl)-2-methylpropanoate (43 g) in tetrahydrofuran was added to lithium aluminium hydride (220 ml of a 1M solution in ether) with stirring at −40° C. After 1 hour the solution was cooled to −70° C., diluted with ether, and treated with brine via dropwise addition, initially at −70° C. and then at −30° C. After warming to room temperature the organic layer was dried (magnesium sulphate), evaporated and the residue purified by dry column chromatography on silica gel eluting with dichloromethane to give 2-(2,3-dihydro-6-methyl-4-oxo-5-phenyl-4H-1,3-oxazin-3-yl)-2-methylpropionaldehyde as a cream solid (22.5 g), NMR $^1$H δ1.35(s,6H), 1.95(s,3H), 5.25(s,2H), 7.22–7.38(m,5H), 9.42(s,1H).

By proceeding in a similar manner the following compounds were also prepared:

2-[5-(2-fluorophenyl)-2,3-dihydro-6-methyl-4-oxo-4H-1, 3-oxazin-3-yl]-2-methylpropionaldehyde as a white solid, NMR $^1$H δ1.38(s,6H), 1.93(s,3H), 4.29(s,2H), 7.74(m,4H), 9.42(s,1H);

2-[2,3-dihydro-6-methyl-4-oxo-5-(2-thienyl)-4H-1,3-oxazin-3-yl]-2-methylpropionaldehyde, NMR 1.38(s,6H), 2.12(s,3H), 5.22(s,2H), 7.0(m,2H), 7.3(m,1H), 9.42(s,1H); and 2-[2,3 -dihydro-5-(2-methoxyphenyl)-6-methyl-4-oxo-4H-1,3-oxazin-3-yl]-2-methylpropionaldehyde, NMR 1.35 (s,6H), 1.85(s,3H), 3.8(s,3H), 5.25(s,2H), 6.9–7.3(m,4H), 9.4(s,1H).

REFERENCE EXAMPLE 2

A mixture of 5-(2-fluorophenyl)-2,2-dimethyl-6-methyl-4H-1,3-dioxin-4-one (2.0 g) and ethyl 2-(N-methyleneamino)-2-methylpropionate (1.45 g) was heated under reflux in xylene for 10 hours. After evaporation to dryness the residue was purified by dry column chromatography on silica gel eluting with cyclohexane/ethyl acetate to give ethyl [5-(2-fluorophenyl)-2,3-dihydro-6-methyl-4-oxo-4H-1,3-oxazin-3-yl]-2-methylpropanoate as a pale yellow oil (1.7 g), NMR 1.24(t,3H), 1.42(s,6H), 1.57(s,3H), 4.15 (q,2H), 5.3(s,2H), 7. 74(m,4H).

By proceeding in a similar manner the following compound was prepared: ethyl (2,3-dihydro-6-methyl-4oxo-4H-1,3-oxazin-3-yl)-2-methyl propanoate, NMR 1.2(t,3H), 1.5 (s,6H), 1.98(s,3H), 2.25(m,1H), 4.15(q,2H), 5.16(s,2H).

REFERENCE EXAMPLE 3

A solution of ethyl 2-(N-methyleneamino)-2-methylpropionate (10.3 g) in xylene was added during 1 hour to a solution of ethyl 2-(2-methoxyphenyl)acetoacetate (8.51 g) in xylene whilst heating under reflux. The rate of addition was controlled so as to equal the rate of azeotropic distillation (via a Dean and Stark separator). Additional xylene was then added and distillation continued for 3 hours. The mixture was evaporated in vacuo to give ethyl 2-[2,3-dihydro-5-2-methoxyphenyl)- 6-methyl-4-oxo-4H-1,3-oxazin-3-yl]-2-methylpropanoate (14.1 g), NMR 1.25(t,3H), 1.55(s,6H), 1.8(s,3H), 3.75(s,3H), 4.15(m,2H), 5.3(s,2H), 6.9–7.3(m,4H).

REFERENCE EXAMPLE 4

A mixture of ethyl 2-methoxyphenyiacetate (11.6 g), sodium tert-butoxide (12.7 g) and ethyl acetate (15.8 g) in diisopropylether was heated at 70° C. for 2.5 hours and stirred at room temperature overnight. Ethyl acetate and hydrochloric acid (2M) were added and the organic phase dried (magnesium sulphate) and evaporated. The residue was distilled in vacuo to give ethyl 2-(2-methoxyphenyl) acetoacetate as a liquid (8.5 g), NMR 1.15 and 1.13(t,3h), 1.8 and 2.2(s,3H), 3.75 and 3.85(s,3H), 4.1–4.3(2q,2H), 5.15(s,1H), 6.9–7.3(m,4H), 13.1(s,1H).

REFERENCE EXAMPLE 5

A mixture of ethyl 2-(2,3-dihydro-5-iodo-6-methyl-4-oxo-4H-1,3-oxazin-3-yl)-2-methylpropanoate (30.0 g), 2-(tributylstannyl)thiophene (33.5 ml), palladium bis-triphenylphosphine chloride (3.08 g) and lithium chloride (20.5 g) in tetrahydrofuran was heated at 50° C. for 24 hours. Further 2-(tributylstannyl)thiophene (2.8 ml) was added and the mixture heated for a further 18 hours. Palladium bis-triphenylphosphine chloride (0.62 g) was added and heating continued for 18 hours. The mixture was poured into water, extracted (ether) and the organic phase washed (brine), dried (magnesium sulphate) and evaporated. Purification by chromatography on silica gel gave ethyl [2,3-dihydro-6-methyl-4-oxo-5-(2-thienyl)-4H-1,3-oxazine-3-yl]-2-methylpropanoate (14.5 g), NMR 1.15(t,3H), 1.55(s,6H), 2.1(s,3H), 4.15(q,2H), 5.25(s,2H), 6.9–7.4(m,3H).

REFERENCE EXAMPLE 6

N-Iodosuccinimide (238 g) was added to a stirred solution of ethyl 2-(2,3-dihydro-6-methyl-4-oxo-4H-1,3-oxazin-3-yl)-2-methylpropanoate (200 g) in acetic acid. The mixture was stirred at 40–45° C. for 5 hours then at ambient temperature overnight and evaporated. The residue was diluted with ether, washed with water, sodium carbonate solution (2M) and brine, dried (MgSO4) and evaporated. A solution of the residue in ethanol was cooled to −40° C. to give ethyl 2-(2,3-dihydro-5-iodo-6-methyl-4-oxo-4H-1,3-oxazin-3-yl)-2-methylpropanoate (66.9 g), m.p. 85–87° C.

According to a further feature of the present invention, there are provided compositions suitable for herbicidal use comprising one or more of the 1,3-oxazin-4-one derivatives of formula I or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkvl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, microfine silicon dioxide, talc, chalk, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, giinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, glycol ethers, tetrahydrofurfuryl alcohol, acetophenone, cyclohexanone, isophorone, N-alkyl pyrrolidones, toluene, xylene, mineral, animal and vegetable oils, esterified vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of such concentrates to water producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, spreading agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are

- aqueous suspension concentrates which comprise from 10 to 70% of one or more compounds of formula I, from 2 to 10% of surface-active agent, from 0.1 to 5% of thickener and from 15 to 87.9% of water,
- wettable powders which comprise from 10 to 90% of one or more compounds of formula I, from 2 to 10% of surface-active agent and from 8 to 88% of solid diluent or carrier;
- water soluble or water dispersible powders which comprise from 10 to 90% of one or more compounds of formula I, from 2 to 40% of sodium carbonate and from 0 to 88% of solid diluent;
- liquid water soluble concentrates which comprise from 5 to 50%, e.g. 10 to 30%, of one or more compounds of formula I, from 0 to 25% of surface-active agent and from 10 to 90%, e.g. 45 to 85%, of water miscible solvent, e.g. triethylene glycol, or a mixture of water-miscible solvent and water;
- liquid emulsifiable suspension concentrates which comprise from 10 to 70% of one or more compounds of formula I, from 5 to 15% of surface-active agent, from 0.1 to 5% of thickener and from 10 to 84.9% of organic solvent, e.g. mineral oil;
- water dispersible granules which comprise from 1 to 90%, e.g. 25 to 75% of one or more compounds of formula I, from 1 to 15%, e.g. 2 to 10%, of surface-active agent and from 5 to 95%, e.g. 20 to 60%, of solid diluent, e.g. clay, granulated with the addition of water to form a paste and then dried and
- emulsifiable concentrates which comprise 0.05 to 90%, and preferably from 1 to 60% of one or more compounds of formula I, from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described.

Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxyacetic acid], dicamba [3,6-dichloro-2-methoxybenzoic acid], difenzoquat [1,2-dimethyl-3,5-diphenyl-pyrazolium salts], flampropmethyl [methyl N-2-(N-benzoyl-3-chloro-4-fluoroanilino)-propionate], fluometuron [N'-(3-trifluoromethylphenyl)N,N-dimethylurea], isoproturon [N'-(4-isopropylphenyl)-N,N-dimethylurea], diclofop {(RS-2-[4-2,4-dichlorophenoxy)phenoxy]propionic acid}, fenoxaprop and fenoxaprop-P {2-[4-(6-chloro-1,3-benzoxazol-2-yloxy)phenoxy]propionic acid }, diflufenican{N-(2,4-difluorophenyl)-2-[3-(trifluoromethyl)phenoxy]-3-pyridinecarboxamide}, tralkoxydim {2-[1-(ethoxyimino)propyl]-3-hydroxy-5-mesitylcyclohex-2-enone}, clodinafop {2-[4-(5-chloro-3-fluoro-2-pyridyloxy)phenoxy]propionic acid}, sulcotrione [2-(2-chloro-4-methylsulphonylbenzoyl)cyclohexane-1,3-dione], flurtamone {5-methylamino-2-phenyl-4-[3-(trifluoromethyl)phenyl]-3(2H)-furanone}, aclonifen (2-chloro-6-nitro-3-phenoxyaniline), and sulfonylureas (e.g. nicosulfuron);

- insecticides, e.g. synthetic pyrethroids, e.g. permethrin and cypermethrin,
- and fungicides, e.g. carbamates, e.g. methyl N-(1-butyl-carbamoyl-benzimidazol-2-yl)carbamate, and triazoles e.g. 1-(4chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the 1,3-oxazin-4-one derivative of formula I or, as is preferred, a herbicidal composition as hereinbefore described, and preferably a herbicidal concentrate which must be diluted before use, comprising at least one of the 1,3-oxazin-4-one derivative of formula I within a container for the aforesaid derivative or derivatives of formula I, or a said herbicidal composition, and instructions physically associated with the aforesaid container setting out the manner in which the aforesaid derivative or derivatives of formula I or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal or sacks. The containers will normally be of sufficient capacity to contain amounts of the 1,3-oxazin-4-one derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.5 g and 5000 g of active material per hectare in the manner and for the purposes hereinbefore described.

The following Examples illustrate herbicidal compositions according to the present invention. The following trade marks appear in the description: Ethylan, Soprophor, Sopropo, Rhodorsil, Atagel, Synperonic, Solvesso, Arkopon, Tixosil.

| Example C1: | |
|---|---|
| A suspension concentrate is formed from: | |
| Oxazinone derivative (Compound 1) | 20% |
| Ethylan BCP (surfactant) | 0.5% |
| Soprophor FL | 0.5% |
| Sopropon T36 (Dispersant) | 0.2% |
| Rhodorsil 426R (Antifoaming agent) | 0.01% |
| Propylene glycol (antifreeze) | 5.0% |
| Atagel 50 (anti-settling agent) | 2.0 |
| Water | to 100% |

Similar suspension concentrates may be prepared by replacing Compound I with other oxazinone derivatives of formula I.

| Example C2 | |
|---|---|
| An emulsion concentrate is formed from the following: | |
| Oxazinone derivative (Compound 1) | 10% |
| Synperonic NPE1800 (surfactant) | 4.9% |
| Arylan CA (surfactant) | 5.0% |
| Cyclohexanone (solvent) | 9.8% |
| NMP (solvent) | 9.8% |
| Solvesso 150 (blending agent) | 5.0% |
| Water | to 100% |

Note: NMP means N-methylpyrrolidine

Similar emulsion concentrates may be prepared by replacing Compound 1 with other oxazinone derivatives of formula I.

| Example C3 | |
|---|---|
| A wettable powder is formed from the following: | |
| Oxazinone derivative (Compound 1) | 20.0% |
| Arylan SX flake (surfactant) | 3.0% |
| Arkopon T (surfactant) | 5.0% |
| Sodium polycarboxylate (dispersant) | 1.0% |
| Tixosil 38 (flow aid) | 3.0% |
| China Clay | 68.0% |

Similar wettable powders may be prepared by replacing Compound 1 with other oxazinone derivatives of formula I.

According to a feature of the present invention, there is provided a method for controlling the growth of weeds (i.e. undesired vegetation) at a locus which comprises applying to the locus a herbicidally effective amount of at least one 1,3-oxazin-4-one derivative of formula I or an agriculturally acceptable salt thereof For this purpose, the 1,3-oxazin-4-one derivatives are normally used in the form of herbicidal compositions (i.e. in association with compatible diluents or carriers and/or surface active agents suitable for use in herbicidal compositions), for example as hereinafter described.

The compounds of formula I show herbicidal activity against dicotyledonous (i.e. broad-leafed) and monocotyledonous (e.g. grass) weeds by pre- and/or post-emergence application. In particular the compounds show interest in the control of *Echinochloa crus-galli* with selectivity in rice.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium* and grass weeds, for example *Alopecurus myosuroides, Avena fatua, Digitaria sanguinalis, Echinochloa crus-galli, Eleusine indica* and Setaria spp, e.g. *Setaria faberii* or *Setaria viridis,* and sedges, for example, *Cyperus esculentus.*

The amounts of compounds of formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 1 g and 1000 g of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 10 g and 500 g, and preferably between 25 g and 250 g, of active material per hectare are particularly suitable.

The compounds of the invention are especially useful for controlling grass weed species.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 50 g and 5000 g, and preferably between 50 g and 2000 g, most preferably between 100 g and 1000 g of active material per hectare.

The compounds of formula I may also be used to control the growth of weeds, especially those indicated above, at loci which are not crop-growing areas but in which the control of weeds is nevertheless desirable.

Examples of such non-crop-rowing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 50 g and 5000 g, and preferably between 50 g and 2000 g, most preferably between 100 g and 1000 g of active material per hectare are particularly suitable for this purpose.

When used to control the growth of weeds by pre-emergence application, the compounds of formula I may be incorporated into the soil in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a pre-emergence control on later-germinating weeds in the soil.

Where especially prolonged weed control is required, the application of the compounds of formula I may be repeated if required.

METHOD OF USE OF HERBICIDAL COMPOUNDS

TEST METHOD (A)

a) General

Appropriate quantities of the compounds used to treat the plants were dissolved in acetone to give solutions equivalent to application rates of up to 1000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | Approx number of seeds/pot |
| --- | --- |
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | Number of plants per pot | Growth stage |
| --- | --- | --- |
| 1) Broad leafed weeds | | |
| Abutilon theophrasti | 3 | 1–2 leaves |
| Amaranthus retroflexus | 4 | 1–2 leaves |
| Galium aparine | 3 | $1^{st}$ whorl |
| Ipomoea purpurea | 3 | 1–2 leaves |
| Sinapis arvensis | 4 | 2 leaves |
| Xanthium strumarium | 1 | 2–3 leaves. |
| 2) Grass weeds | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Cyperus esculentus | 3 | 3 leaves. |

| Crops | Number of plants per pot | Growth stage |
| --- | --- | --- |
| 1) Broad leafed Crops | | |
| Cotton | 2 | 1 leaf |
| Soya | 2 | 2 leaves. |
| 2) Grass Crops | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

TEST METHOD B a) General

As in Test Method A above but the solutions were applied from an automated sprayer delivering the equivalent of 720 liters of spray fluid per hectare.

b) Weed control: Pre-emergence

The seeds were sown in 70 mm square, 75 mm deep plastic pots in non-sterile soil 3 species per pot. The quantities of seed per pot were as follows:

| Weed species | Approx number of seeds/species |
| --- | --- |
| 1) Broad-leafed weeds | |
| Abutilon theophrasti | 7–8 |
| Amaranthus retroflexus | 20 (pinch) |
| Galium aparine | 4–5 |
| Ipomoea purpurea | 5 |
| Sinapis arvensis | 7–8 |
| Matricaria inodora | 20 (pinch) |
| Stellaria media | 20 (pinch) |
| 2) Grass weeds | |
| Alopecurus myosuroides | 15–20 |
| Avena fatua | 10 |
| Echinochloa crus-galli | 15 |
| Setaria viridis | 15 |
| Setaria faberii | 15 |
| Apera spica-venti | 20 (pinch) |

| Crop | |
| --- | --- |
| 1) Broad-leafed | |
| Cotton | 3 |
| Soya | 2 |
| 2) Grass | |
| Maize | 2 |
| Rice | 5 |
| Wheat | 5 |

The compounds of the invention were applied to the soil surface, containing the seeds, as described in (a). Pots containing the species represented were allocated to each treatment, with unsprayed controls and controls sprayed with acetone alone.

After treatment the pots were placed on capillary matting kept in a glass house, and watered overhead. Visual assessment of crop damage was made 17 days after spraying. The results were expressed as the percentage reduction in growth or damage to the crop or weeds, in comparison with the plants in the control pots.

TEST METHOD C

Paddy post-emergence application in greenhouse

Paddy field soil was filled in 170 $cm^2$ plastic pots, a suitable amount of water and chemical fertilisers were added thereto and kneaded to convert it to a state of a paddy.

Paddy rice plants (variety; Koshihikari), that had been grown in advance in a greenhouse to a stage of two leaves, were transplanted to each pot (two seedlings per pot). Then in each pot there were sown predetermined amounts of seeds of *Echinochloa oryzicola, Monochoria vaginalis, Lindernia procumbens* and *Scirpus juncoides* respectively, and water was added to a depth of 3 cm.

After having grown the plants in a greenhouse until *Echinochloa oryzicola* reached a stage of 1.5 leaves, solutions were prepared in 100% acetone using compounds described in the Examples so that they contained active ingredients in an amount equivalent to 75, 300 and 1200 g/ha. The solutions were applied by dropping with a pipette.

After 21 days from the application with the chemicals, herbicidal effects on each weed and phytotoxicity on paddy rice plants were visually assessed, and the results expressed as the percentage reduction in growth or damage to the crop or weeds in comparison with the plants in the control pots.

When applied at 1000 g/hectare or less preemergence in Test Method A, compounds 1–6, 9–21, 27–36, 38, 39, 43, 56, 90–111, 114–116, 118–123 of the invention gave at least 80% reduction in growth of one or more of the weed species listed above; at levels of applications toxic to the weeds these compounds were selective in at least one crop species.

When applied at 1000 g/hectare or less pre-emergence in Test Method B compounds 7 and 8 of the-invention gave at least 90% reduction in growth of one or more of the weed species listed above.

When applied at 1000 g/hectare or less post-emergence in Test Method A, compounds 1, 2, 5, 6, 15, 16 and 18 of the invention gave at least 80% reduction in growth of one or more of the weed species listed above; at levels of applications toxic to the weeds these compounds were selective in at least one crop species.

When applied at 1200 g/hectare or less, in Test Method C, compounds 1–10, 13–21, 27–36, 39, 43, 48, 56, 90, 91, 93–100, 102, 104–109, 111–114, and 116–123 and of the invention gave at least 80% reduction in growth of one or more of the weed species listed above.

What is claimed is:

1. A 1,3-oxazin-4-one of formula (I):

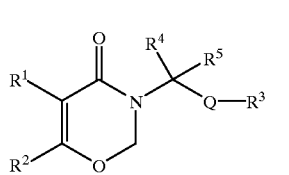

(I)

wherein:

$R^1$ represents phenyl optionally substituted by from one to five groups which may be the same or different selected from halogen, hydroxy, lower alky, lower haloalkyl, lower alkoxy, lower haloalkoxy, —S(O)$_n$R$^7$, —CO$_2$R$^7$, —COR$^7$, cyano, nitro, —O(CH$_2$)$_q$CO$_2$R$^7$ and phenoxy;

a five to seven membered heteroaromatic ring having from one to four ring heteroatoms which may be the same or different selected from nitrogen, oxygen and sulphur, said ring being optionally substituted by from one to four groups which may be the same or different selected from halogen, hydroxy, lower alkyl, lower haloalkyl, lower alkoxy, lower haloalkoxy, —S(O)$_n$R$^7$, —CO$_2$R$^7$, —COR$^7$, cyano, nitro, —O(CH$_2$)$_q$CO$_2$R$^7$ and phenoxy;

or a straight- or branched-chain optionally halogenated alkyl, alkenyl or alkynyl group containing up to ten carbon atoms;

$R^2$ represents:

a hydrogen atom; or a straight- or branched-chain alkyl group containing from one to ten carbon atoms which is optionally substituted by one or more groups $R^8$ which may be the same or different;

a straight- or branched-chain optionally halogenated alkenyl or alkynyl group having up to ten carbon atoms;

or a group selected from cyano, —CHO, —COR$^7$, —CO$_2$H, —CO$_2$R$^7$, —COSR$^7$, —CONR$^9$R$^{10}$, —CH=NOH, —CH=NOR$^7$, —CH=NOCOR$^7$, —CH=NNR$^9$R$^{10}$, —CH$_2$CN, —CH$_2$NO$_2$ and oxiranyl;

$R^3$ represents —(CH$_2$)$_r$—(phenyl or naphthyl optionally substituted by from one to five groups which may be the same or different selected from halogen, hydroxy, lower alkyl, lower haloalkyl, lower alkoxy, lower haloalkoxy, —S(O)$_n$R$^6$, —CO$_2$R$^6$, —COR$^6$, cyano, nitro, —O(CH$_2$)$_q$CO$_2$R$^6$, phenoxy, and —SF$_5$);

a —(CH$_2$)$_s$— (five, to seven membered heteroaromatic ring having from one to four ring heteroatoms which may be the same or different selected from nitrogen, oxygen and sulphur, said ring being optionally fused to a phenyl ring or to a second five to seven membered heteroaromatic ring having from one to four heteroatoms which may be the same or different selected from nitrogen, oxygen and sulphur, to form a bicyclic ring system the monocyclic ring or either ring in the bicyclic system being optionally substituted by from one to four groups which may be the same or different selected from halogen, hydroxy, lower alkyl, lower haloalkyl, lower alkoxy, lower haloalkoxy, —S(O)$_n$R$^6$, —CO$_2$R$^6$, —COR$^6$, cyano, nitro, —O(CH$_2$)$_q$CO$_2$R$^6$ and phenoxy);

a straight- or branched-chain optionally halogenated alkyl, alkenyl or alkynyl group containing up to ten carbon atoms;

a straight- or branched-chain optionally halogenated alkyl, alkenyl or alkynyl group containing up to ten carbon atoms which is substituted by cycloalkyl containing from three to six carbon atoms; or cycloalkyl containing from three to six carbon atoms or cycloalkenyl containing five or six carbon atoms, the ring systems of which are optionally substituted by a group $R^6$ or one or more halogen atoms which may be the same or different;

$R^4$ and $R^5$ independently represent lower alkyl;

$R^6$ and $R^7$ independently represent lower alkyl or lower haloalkyl;

n represents zero, one or two;

q represents one or two;

r represents zero, one or two; s represents zero or one;

$R^8$ is halogen, —OH, —OR$^7$, —OCOR$^7$, —S(O)$_n$R$^7$, —NR$^9$R$^{10}$ or azide;

$R^9$ and $R^{10}$ independently represent hydrogen, lower alkyl or lower haloalkyl;

Q represents —C(=O)—, —CH(OH)— or —C(OR$^{11}$)(OR$^{11}$)—, in which $R^{11}$ represents lower alkyl; or the two groups —OR$^{11}$, together with the carbon atom to which they are attached, form a five or six membered cyclic ketal group;

or an agriculturally acceptable salt thereof.

2. A 1,3-oxazin-4-one of formula (I) as defined in claim 1 in which:

$R^1$ represents phenyl optionally substituted by from one to five groups which may be the same or different selected from halogen, hydroxy, lower alkyl, lower haloalkyl, lower alkoxy, lower haloalkoxy, —S(O)$_n$R$^7$, —CO$_2$R$^7$, —COR$^7$, cyano, nitro, —O(CH$_2$)$_q$CO$_2$R$^7$ and phenoxy; or a five to seven membered heteroaromatic ring having from one to four ring heteroatoms which may be the same or different selected from nitrogen, oxygen and sulphur, said ring being optionally substituted by from one to four groups which may be the same or different selected from halogen, hydroxy, lower alkyl lower haloalkyl, lower alkoxy, lower haloalkoxy, —S(O)$_n$R$^7$, —CO$_2$R$^7$, —COR$^7$, cyano, nitro, —O(CH$_2$)$_q$CO$_2$R$^7$ and phenoxy; or a straight- or branched-chain optionally halogenated al, alkenyl or alkynyl group containing up to ten carbon atoms;

$R^2$ represents:

a hydrogen atom; or a straight- or branched-chain alkyl group containing from one to ten carbon atoms which is optionally substituted by one or more groups $R^8$ which may be the same or different;

a straight- or branched-chain optionally halogenated alkenyl or alkynyl group having up to ten carbon atoms; or a group selected from cyano, —CHO, —COR$^7$, —CO$_2$H, —CO$_2$R$^7$, —COSR$^7$, —CONR$^9$R$^{10}$, —CH═NOH, —CH═NOR$^7$, —CH═NOCOR$^7$, —CH═NNR$^9$R$^{10}$, —CH$_2$CN, —CH$_2$NO$_2$ and oxiranyl;

R$^3$ represents —(CH$_2$)$_r$—(phenyl optionally substituted by from one to five groups which may be the same or different selected from halogen, hydroxy, lower alkyl, lower haloalkyl, lower alkoxy, lower haloalkoxy, —S(O)$_n$R$^6$, —CO$_2$R$^6$, —COR$^6$, cyano, nitro, —O(CH$_2$)$_q$CO$_2$R$^6$ and phenoxy);

—(CH$_2$)$_s$—(five to seven membered heteroaromatic ring having from one to four ring heteroatoms which may be the same or different selected from nitrogen, oxygen and sulphur, said ring being optionally fused to a phenyl ring or to a second five to seven membered heteroaromatic ring having from one to four heteroatoms which may be the same or different selected from nitrogen, oxygen and sulphur, to form a bicyclic ring system the monocyclic ring or either ring in the bicyclic system being optionally substituted by from one to four groups which may be the same or different selected from halogen, hydroxy, lower alkyl, lower haloalkyl, lower alkoxy, lower haloalkoxy, —S(O)$_n$R$^6$, —CO$_2$R$^6$, —COR$^6$, cyano, nitro, —O(CH$_2$)$_q$CO$_2$R$^6$ and phenoxy); or a straight- or branched-chain optionally halogenated alkyl, alkenyl or alkynyl group containing up to ten carbon atoms; or cycloalkyl containing from three to six carbon atoms which is optionally substituted by a group R$^6$ or one or more halogen atoms which may be the same or different;

R$^4$ and R$^5$ independently represent lower alkyl;

R$^6$ and R$^7$ independently represent lower alkyl or lower haloalkyl;

n represents zero, one or two;

q represents one or two;

r represents zero or one; s represents zero or one;

R$^8$ is a group selected from halogen, —OH, —OR$^7$, —OCOR$^7$, —S(O)$_n$R$^7$ and —NR$^9$R$^{10}$;

R$^9$ and R$^{10}$ independently represent hydrogen, lower alkyl or lower haloalkyl;

Q represents —C(═O)—, —CH(OH)— or —C(OR$^{11}$)(OR$^{11}$)—; in which R$^{11}$ represents lower alky; or the two groups —OR$^{11}$, together with the carbon atom to which they are attached, form a five or six membered cyclic ketal group;

or an agriculturally acceptable salt thereof.

3. A compound according to claim 1 in which R$^1$ represents phenyl or thienyl optionally substituted by one to five groups selected from halogen, lower alkyl and lower haloalkyl.

4. A compound according to claim 3 in which R$^1$ represents phenyl.

5. A compound according to claim 1 in which R$^2$ represents a straight- or branched-chain alkyl group having from one to six carbon atoms.

6. A compound according to claim 5 in which R$^2$ represents methyl.

7. A compound according to claim 1 in which R$^4$ and R$^5$ each represent methyl.

8. A compound according to claim 1 in which Q represents —C(═O)—.

9. A compound according to claim 1 in which R$^3$ is cyclopentyl.

10. A compound according to claim 1 in which R$^3$ is n-butyl or butenyl.

11. A compound according to claim 2 in which:

R$^1$ represents;

phenyl optionally substituted by halogen;

R$^2$, R$^4$ and R$^5$ each represent methyl;

Q represents —C(═O)—;

R$^3$ represents:

—(CH$_2$)$_r$—(phenyl optionally substituted by one or two groups selected from halogen and an optionally halogenated alkyl group containing one or two carbon atoms);

or a straight- or branched-chain alkyl, alkenyl or alkynyl group containing up to four carbon atoms;

and r is zero or one.

12. A compound according to claim 2 in which:

R$^1$ represents:

phenyl or thienyl optionally substituted by halogen or methyl;

R$^2$, R$^4$ and R$^5$ each represent methyl;

Q represents —C(═O)—;

R$^3$ represents —(CH$_2$)$_r$—(phenyl optionally substituted by one or two groups selected from halogen or an optionally halogenated alkyl group containing one or two carbon atoms);

a straight- or branched-chain allyl or alkenyl group containing up to six carbon atoms;

or cycloalkyl containing from three to six carbon atoms;

and r is zero or one.

13. A compound according to claim 1 having at least one feature selected from the group consisting of:

R$^1$ represents phenyl or thienyl optionally substituted by halogen or methoxy;

R$^2$, R$^4$ and R$^5$ each represent methyl;

Q represents —C(═O)—;

R$^3$ represents —(CH$_2$)$_r$—(phenyl optionally substituted by one or two groups selected from halogen or methyl);

a thienyl, furyl, benzothiazolyl or pyridyl, optionally substituted by halogen, or (optionally halogenated) methyl;

a straight- or branched-chain optionally halogenated allyl, alkenyl or alknyl group containing up to eight carbon atoms; or cycloalkyl containing from three to six carbon atoms; and r is zero or one.

14. A compound according to claim 1 which is:

2-(2,3-dihydro-6-methyl-4oxo-5-phenyl-4H-1,3-oxazin-3-yl)-2,4-dimethylpentan-3-one;

2-(2,3-dihydro-6-methyl-4-oxo-5-phenyl-4H-1,3)-oxazin-3-yl)-2 methylheptan-3-one;

1-(3,5-difluorophenyl)-2-(2,3-dihydro-6-methyl-4-oxo-5-phenyl-4H-1,3-oxazin-3-yl)-2-methylpropan-1-one;

1-(2-fluoro-5-trifluoromethylphenyl)-2-2,3-dihydro-6-methyl-4-oxo-5-phenyl-4H-1,3-oxazin-3-yl)-2-methylpropan-1-one;

1-(3-chlorophenyl)-3-(2,3-dihydro-6-methyl-4-oxo-5-phenyl-4H-1,3-oxazin-3-yl)-3-methylbutan-2-one;

1-(3-trifluoromethylphenyl)-3-(2,3-dihydro-6-methyl-4-oxo-5-phenyl-4H-1,3-oxazin-3-yl)-3-methylbutan-2-one;

2-(2,3-dihydro-6-methyl-4-oxo-5-phenyl-4H-1,3-oxazin-3-yl)-2-methylhex-5-en-3-one;

4-(2,3-dihydro-6-methyl-4-oxo-5-phenyl-4H-1,3-oxazin-3-yl)-4-methylpent-1-en-3-one;

1-(4-fluorophenyl)-2-[5-(2-fluorophenyl)-2,3-dihydro-6-methyl-4-oxo-4H-1,3-oxazin-3-yl]-2-methylpropan-1-one;

4-(2,3-dihydro-6-methyl-4-oxo-5-phenyl-4H-1,3-oxazin-3-yl)-4-methylpent-1-yn-3-one;

2-[5-(2-fluorophenyl)-2,3-dihydro-6-methyl-4-oxo-4H-1,3-oxazin-3-yl]-1-(2-methylphenyl)-2-methylpropan-1-one;

1-(4-fluoro-3-methylphenyl)-2-[5-(2-fluorophenyl)-2,3-dihydro-6-methyl-4-oxo-4H-1,3-oxazin-3-yl]-2-methylpropan-1-one;

2-(2,3-dihydro-6-methyl-4-oxo-5-phenyl-4H-1,3-oxazin-3-yl)-2-methyl-1-(2-methylphenyl)propan-1-one;

1-(4-fluorophenyl)-2-(2,3-dihydro-6-methyl-4-oxo-5-phenyl-4H-1,3-oxazin-3-yl)-2-methylpropan-1-one;

1-4-fluoro-3-methylphenyl)-2-(2,3-dihydro-6-methyl-4-oxo-5-phenyl-4H-1,3-oxazin-3-yl)-2-methylpropan-1-one;

2-(2,3-dihydro-6-methyl-4-oxo-5-phenyl-4H-1,3-oxazin-3-yl)-2-methyl-1-phenylpropan-1-one;

1-(2-chlorophenyl)-2-(2,3-dihydro-6-methyl-4-oxo-5-phenyl-4H-1,3-oxazin-3-yl)-2-methylpropan-1-one;

1-(3-chlorophenyl)-2-(2,3-dihydro-6-methyl-4-oxo-5-phenyl-4H-1,3-oxazin-3-yl)-2-methylpropan-1-one;

1-(4chlorophenyl)-2-(2,3-dihydro-6-methyl-4-oxo-5-phenyl-4H-1,3-oxazin-3-yl)-2-methylpropan-1-one;

1-(3-trifluoromethylphenyl)-2-(2,3-dihydro-6-methyl-4-oxo-5-phenyl-4H-1,3-oxazin-3-yl)-2-methylpropan-1-one; or 1-(3,5-dichlorophenyl)-2-(2,3-dihydro-6-methyl-4-oxo-5-phenyl-4H-1,3-oxazin-3-yl)-2-methylpropan-1-one.

3-(2,3-dihydro-6-methyl-4-oxo-5-phenyl-4H-1,3-oxazin-3-yl)-3-methylbutan-2-one;

2-(2,3-dihydro-6-methyl-4-oxo-5-phenyl-4H-1,3-oxazin-3-yl)-2-methylhexan-3-one;

2-(2,3-dihydro-6-methyl-4-oxo-5-phenyl-4H-1,3-oxazin-3-yl)-2,5-dimethylhexan-3-one;

2-(2,3-dihydro-6-methyl-4-oxo-5-phenyl-4H-1,3-oxazin-3-yl)-2-methylpentan-3-one;

2-(2,3-dihydro-6-methyl-4-oxo-5-phenyl-4H-1,3-oxazin-3-yl)-2-methylundecan-3-one;

2-(2,3-dihydro-6-methyl-4-oxo-5-phenyl-4H-1,3-oxazin-3-yl)-2,4-dimethylhexan-3-one;

1-cyclopropyl-2-(2,3-dihydro-6-methyl-4-oxo-5-phenyl-4H-1,3-oxazin-3-yl)-2-methylpropan-1-one;

2-(2,3-dihydro-6-methyl-4-oxo-5-phenyl-4H-1,3-oxazin-3-yl)-2,4,4-trimethylpentan-3-one;

2-(2,3-dihydro-6-methyl4-oxo-5-phenyl-4H-1,3-oxazin-3-yl)-2-methyl-1-(2-thienyl)propan-1-one;

2-(2,3-dihydro-6-methyl-4-oxo-5-phenyl-4H-1,3-oxazin-3-yl)-1-(3-furyl)-2-methylpropan-1-one;

1-(2-benzthiazolyl)-2-(2,3-dihydro-6-methyl-4-oxo-5-phenyl-4H-1,3-oxazin-3-yl)-2-methylpropan-1-one;

1-(3,4-dichlorophenyl)-3-2,3-dihydro-6-methyl-4-oxo-5-phenyl-4H-1,3-oxazin-3-yl)-3-methylbutan-2-one;

1-(3,5-dichlorophenyl)-3-(2,3-dihydro-6-methyl-4-oxo-5-phenyl-4H-1,3-oxazin-3-yl)-3-methylbutan-2-one;

3-(2,3-dihydro-6-methyl-4oxo-5-phenyl-4H-1,3-oxazin-3-yl)-1-(3,5-dimethylphenyl)-3-methylbutan-2-one;

1-(4-chlorophenyl)-3-(2,3-dihydro-6-methyl-4-oxo-5-phenyl-4H-1,3-oxazin-3-yl)-3-methylbutan-2-one;

1-cyclopentyl-2-(2,3-dihydro-6-methyl-4-oxo-5-phenyl-4H-1,3-oxazin-3-yl)-2-methylpropan-1-one;

3-(2,3-dihydro-6-methyl-4-oxo-5-phenyl-4H-1,3-oxazin-3-yl)-3-methyl)-1-(3-methylphenyl)butan-2-one;

2-(2,3-dihydro-6-methyl-4-oxo-5-phenyl-4H-1,3-oxazin-3-yl)-2-methylnonan-3-one;

2-(2,3-dihydro-6-methyl-4-oxo-5-phenyl-4H-1,3-oxazin-3-yl)-2-methyloctan-3-one;

3-(2,3-dihydro-6-methyl-4-oxo-5-phenyl-4H-1,3-oxazin-3-yl)-3-methyl-1-(phenyl)butan-2-one;

1-(3,5-difluorophenyl)-3-(2,3-dihydro-6-methyl-4-oxo-5-phenyl-4H-1,3-oxazin-3-yl)-3-methylbutan-2-one;

2-(2,3-dihydro-6-methyl-4-oxo-5-phenyl-4H-1,3-oxazin-3-yl)-2-methyl-1-(6-methylpyrid-2-yl)propan-1-one;

2-(2,3-dihydro-6-methyl-4-oxo-5-phenyl-4H-1,3-oxazin-3-yl)-2,6-dimethylheptan-3-one;

2-(2,3-dihydro-6-methyl-4-oxo-5-phenyl-4H-1,3-oxazin-3 -yl)-2-methyl-1-(4-trifluoromethylpyrid-2-yl)propan-1-one;

1-(2,5-difluorophenyl)-3-(2,3-dihydro-6-methyl-4-oxo-5-phenyl-4H-1,3-oxazin-3-yl)-3-methylbutan-2-one;

1-(2-chlorophenyl)-3-2,3-dihydro-6-methyl-4-oxo-5-phenyl-4H-1,3-oxazin-3-yl)-3-methylbutan-2-one;

1-(2,4-difluorophenyl)-3-(2,3-dihydro-6-methyl-4-oxo-5-phenyl-4H-1,3-oxazin-3-yl)-3-methylbutan-2-one;

1-(4-fluorophenyl)-3-(2,3 -dihydro-6-methyl-4-oxo-5-phenyl-4H-1,3-oxazin-3-yl)-3-methylbutan-2-one;

2-(2,3-dihydro-6-methyl-4oxo-5-phenyl-4H-1,3-oxazin-3-yl)-2-methylhept-6-en-3-one;

2-(2,3-dihydro-6-methyl-4-oxo-5-phenyl-4H-1,3-oxazin-3-yl)-2,4-dimethylheptan-3-one;

2-[2,3-dihydro-5-(2-fluorophenyl)-6-methyl-4-oxo-4H-1,3-oxazin-3-yl]-2-methylheptan-3-one;

2-(2,3-dihydro-6-methyl-4-oxo-5-phenyl-4H-1,3-oxazin-3-yl)-2-methylhept-5-en-3-one;

-2-[2,3-dihydro-5-(2-fluorophenyl)-6-methyl-4-oxo-4H-1,3-oxazin-3-yl]-2-methylhexan-3-one;

2-[2,3-dihydro-5-(2-methoxyphenyl)-6-methyl-4-oxo-4H-1,3-oxazin-3-yl]-2-methylhexan-3-one;

2-[2,3-dihydro-5-(2-methoxyphenyl)-6-methyl-4-oxo-4H-1,3-oxazin-3-yl]-2-methylheptan-3-one;

2-[2,3-dihydro-5-(2-methoxyphenyl)-6-methyl-4-oxo-4H-1,3-oxazin-3-yl]-2-methylhept-6-en-3-one;

1-cyclohexyl-2-(2,3-dihydro-6-methyl-4-oxo-5-phenyl-4H-1,3-oxazin-3-yl)-2-methylpropan-1-one;

2-[2,3-dihydro-6-methyl-4oxo-5-(2-thienyl)-4H-1,3-oxazin-3-yl]-2-methylhexan-3-one;

2-[2,3-dihydro-6-methyl-4-oxo-5-(2-thienyl)-4H-1,3-oxazin-3-yl]-2-methylheptan-3-one;

2-[2,3-dihydro-6-methyl-4-oxo-5-(2-thienyl)-4H-1,3-oxazin-3-yl]-2-methylheptan-3-one;

2-(2,3-dihydro-6-methyl-4-oxo-5-phenyl-4H-1,3-oxazin-3-yl)-2,5-dimethylheptan-3-one;

2-(2,3-dihydro-6-methyl-4-oxo-5-phenyl-4H-1,3-oxazin-3-yl)-2,6,6-trimethylheptan-3-one;

2-(2,3-dihydro-6-methyl-4-oxo-5-phenyl-4H-1,3-oxazin-3-yl)-4-ethyl-2-methylhecan-3-one;

2-(2,3-dihydro-6-methyl-4-oxo-5-phenyl-4H-1,3-oxazin-3-yl)-2,5,5-trinethylhexan-3-one;

2-[2,3-dihydro-6-methyl-4-oxo-5-(2-thienyl)-4H-1,3-oxazin-3-yl]-2-methylhept-6en-3-one, 1-cyclopentyl-2-[2,3-dihydro-6-methyl-4-oxo-5-(2-thienyl)-4H-1,3-oxazin-3-yl]-2-methylpropan-1-one;

1-cyclobutyl-2-(2,3-dihydro-6-methyl-4-oxo-5-phenyl-4H-1,3-oxazin-3-yl)-2-methylpropan-1-one;

2-(2,3-dihydro-6-methyl-4-oxo-5-phenyl-4H-1,3-oxazin-3-yl)-2-methyl-7,7,7-trifluoroheptan-3-one;

2(2,3-dihydro-6-methyl-4-oxo-5-phenyl-4H-1,3-oxazin-3-yl)-2,6-dimethyloctan-3-one; or 2-(2,3-dihydro-6methyl-4-oxo-5-phenyl-4H-1,3-oxazin-3-yl)-2-methylhept-6-yn-3-one.

15. A herbicidal composition comprising an effective amount of a 1,3-oxazin-4-one according to claim 1 or an agriculturally acceptable salt thereof, in association with an agriculturally acceptable diluent or carrier and/or surface active agent.

16. A method for the control of weeds at a locus which comprises applying to said locus a herbicidally effective amount of a 1,3-oxazin-4-one according to claim 1 or an agriculturally acceptable salt thereof.

17. A method according to claim 16 wherein the locus is an area used, or to be used, for the growing of crops and the 1,3-oxazin-4-one is applied at an application rate of from 0.001 to 1.0 kg/ha.

18. A process for the preparation of a 1,3-oxazin-4-one of formula (I) as defined in claim 1 which comprises:

(a) where Q represents —C(=O)—, oxidizing the corresponding compound of formula (I) in which Q represents —CH(OH)—;

(b) where Q represents —CH(OH)—, reacting an aldehyde of formula (II):

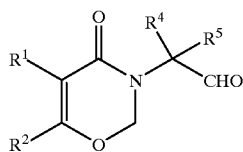

(II)

wherein $R^1$, $R^2$, $R^4$ and $R^5$ are as defined in claim 1, with an organometallic compound of formula $R^3$—M wherein $R^3$ is as defined in claim 1 and M represents a metallic group;

(c) where Q represents —C(OR$^{11}$)(OR$^{11}$)— reacting the corresponding compound of formula (I) wherein Q represents —C(=O)— with an alcohol of formula $R^{11}$—OH wherein $R^{11}$ is as defined in claim 1; or (d) where n is one or two, oxidizng the sulphur atom of the corresponding compound of formula (I) in which n is zero or one;

optionally followed by the conversion of the compound of formula (I) thus obtained into an agriculturally acceptable salt thereof.

19. A compound according to claim 2 in which $R^1$ represents phenyl or thienyl optionally substituted by one or five groups selected from halogen, lower alkyl and lower haloalkyl.

20. A compound according to claim 19 in which $R^1$ represents phenyl.

21. A compound according to claim 2 in which $R^2$ represents a straight- or branched-chain alkyl group having from one to six carbon atoms.

22. A compound according to claim 3 in which $R^2$ represents a straight- or branched-chain alkyl group having from one to six carbon atoms.

23. A compound according to claim 4 in which $R^2$ represents a straight- or branched-chain alkyl group having from one to six carbon atoms.

24. A compound according to claim 19 in which $R^2$ represents a straight- or branched-chain alkyl group having from one to six carbon atoms.

25. A compound according to claim 20 in which $R^2$ represents a straight- or branched-chain alkyl group having from one to six carbon atoms.

26. A compound according to claim 21 in which $R^2$ represents methyl.

27. A compound according to claim 2 in which $R^4$ and $R^5$ each represent methyl.

28. A compound according to claim 2 in which Q represents —C(=O)—.

29. A compound according to claim 2 in which $R^3$ represents cyclopentyl.

30. A compound according to claim 2 in which $R^3$ represents n-butyl or butenyl.

31. A herbicidal composition comprising a herbicidally effective amount of a 1,3-oxazin-4-one according to claim 2 or an agriculturally acceptable salt thereof, in association with an agriculturally acceptable diluent or carrier and/or surface active agent.

32. A herbicidal composition comprising a herbicidally effective amount of a 1,3-oxazin-4-one according to claim 11 or an agriculturally acceptable salt thereof, in association with an agriculturally acceptable diluent or carrier and/or surface active agent.

33. A herbicidal composition comprising a herbicidally effective amount of a 1,3-oxazin-4-one according to claim 12 or an agriculturally acceptable salt thereof, in association with an agriculturally acceptable diluent or carrier and/or surface active agent.

34. A herbicidal composition comprising a herbicidally effective amount of a 1,3-oxazin-4-one according to claim 13 or an agriculturally acceptable salt thereof, in association with an agriculturally acceptable diluent or carrier and/or surface active agent.

35. A herbicidal composition comprising a herbicidally effective amount of a 1,3-oxazin-4-one according to claim 14 or an agriculturally acceptable salt thereof, in association with an agriculturally acceptable diluent or carrier and/or surface active agent.

36. A method for the control of weeds at a locus which comprises applying to said locus a herbicidally effective amount of a 1,3-oxazin-4-one according to claim 2 or an agriculturally acceptable salt thereof.

37. A method for the control of weeds at a locus which comprises applying to said locus a herbicidally effective amount of a 1,3-oxazin-4-one according to claim 11 or an agriculturally acceptable salt thereof.

38. A method for the control of weeds at a locus which comprises applying to said locus a herbicidally effective amount of a 1,3-oxazin-4-one according to claim 12 or an agriculturally acceptable salt thereof.

39. A method for the control of weeds at a locus which comprises applying to said locus a herbicidally effective amount of a 1,3-oxazin-4-one according to claim 13 or an agriculturally acceptable salt thereof.

40. A method for the control of weeds at a locus which comprises applying to said locus a herbicidally effective amount of a 1,3-oxazin-4-one according to claim 14 or an agriculturally acceptable salt thereof.

41. A method according to claim 36 wherein the locus is an area used, or to be used, for the growing of crops and the 1,3-oxazin-4-one is applied at an application rate of from 0.001 to 1.0 kg/ha.

* * * * *